United States Patent
Barenholz et al.

(10) Patent No.: US 10,004,688 B2
(45) Date of Patent: Jun. 26, 2018

(54) LIPOSOMAL MUPIROCIN

(71) Applicant: Yissum Research Development Company of the Hebrew University of Jerusalem Ltd., Jerusalem (IL)

(72) Inventors: Yechezkel Barenholz, Jerusalem (IL); Amiram Goldblum, Tel Aviv (IL); Ahuva Cern, Modiin (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days. days.

(21) Appl. No.: 15/303,131

(22) PCT Filed: Apr. 8, 2015

(86) PCT No.: PCT/IL2015/050376
§ 371 (c)(1),
(2) Date: Oct. 10, 2016

(87) PCT Pub. No.: WO2015/155773
PCT Pub. Date: Oct. 15, 2015

(65) Prior Publication Data
US 2017/0027869 A1  Feb. 2, 2017

Related U.S. Application Data

(60) Provisional application No. 61/977,731, filed on Apr. 10, 2014.

(51) Int. Cl.
*A61K 9/127* (2006.01)
*A61K 31/351* (2006.01)
*A61K 47/40* (2006.01)
*A61K 47/69* (2017.01)

(52) U.S. Cl.
CPC .......... *A61K 9/1271* (2013.01); *A61K 31/351* (2013.01); *A61K 47/40* (2013.01); *A61K 47/6951* (2017.08)

(58) Field of Classification Search
None
See application file for complete search history.

(56) References Cited

U.S. PATENT DOCUMENTS

| | | | | |
|---|---|---|---|---|
| 5,939,096 A * | 8/1999 | Clerc | .............. | A61K 9/1278 424/450 |
| 2006/0110441 A1 * | 5/2006 | Wong | .............. | A61K 9/127 424/450 |
| 2007/0014845 A1 * | 1/2007 | Zhang | .............. | A61K 9/0019 424/450 |
| 2009/0196918 A1 * | 8/2009 | Joguparthi | .............. | A61K 9/0019 424/450 |
| 2009/0304783 A1 * | 12/2009 | Walsh | .............. | A61K 31/351 424/450 |
| 2012/0201874 A1 * | 8/2012 | Li | .............. | A61K 9/0019 424/450 |

FOREIGN PATENT DOCUMENTS

WO  2007/005754 A2  1/2007

OTHER PUBLICATIONS

Cern et al., "Quantitative structure—property relationship modeling of remote liposome loading of drugs", Journal of Controlled Release, vol. 160, pp. 147-157, (2012).
Cern et al., "Computer-aided design of liposomal drugs: In silica prediction and experimental validation of drug candidates for liposomal remote loading", Journal of Controlled Release, vol. 173, pp. 125-131, (2014).
Chen et al., "Drug-in-cyclodextrin-in-liposomes: a promising delivery system for hydrophobic drugs", Expert Opin. Drug Deliv., vol. 11, No. 4, pp. 565-577, (2014).
Clerc et al., "Loading of amphipathic weak acids into liposomes in response to transmembrane calcium acetate gradients", Biochimica et Biophysica Acta, vol. 1240, pp. 257-265, (1995).
Hurler et al., "Improved Burns Therapy: Liposomes-in-Hydrogel Delivery System for Mupirocin", Journal of Pharmaceutical Sciences, vol. 101, No. 10, pp. 3906-3915, (2012).
McCormack et al., "Drugs-in-cyclodextrins-in-liposomes: an approach to controlling the fate of water insoluble drugs in vivo", International Journal of Pharmaceutics, vol. 162, pp. 59-69, (1998).
Noble, "The uses and abuses of mupirocin", Journal of Dermatological Treatment, vol. 1, No. 6, pp. 317-319, (1991).
Zhou et al., "Novel Liposomal Gefitinib (L-GEF) Formulations", Anticancer Research, vol. 32, pp. 2919-2924, (2012).
Zucker et al., "Liposome drugs' loading efficiency: A working model based on loading conditions and drug's physiochemical properties", Journal of Controlled Release, vol. 139, pp. 73-80, (2009).

* cited by examiner

*Primary Examiner* — Celeste A Roney
(74) *Attorney, Agent, or Firm* — Vorys, Sater, Seymour & Pease LLP; Ari Zytcer

(57) ABSTRACT

Provided are liposomes encapsulating mupirocin, with particular benefit for systemic therapeutically effective delivery. Also provided herein are pharmaceutical compositions including the liposomes and methods of using them. The liposomes include a lipid membrane and an intraliposomal compartment, the intraliposomal compartment encapsulating mupirocin, at least one cyclodextrin compound and a pH dependent ionizable anion, e.g. acetate.

18 Claims, 9 Drawing Sheets

Figure 6A
Figure 6B
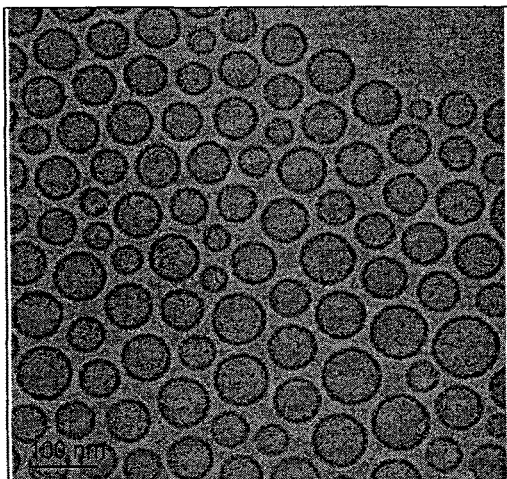
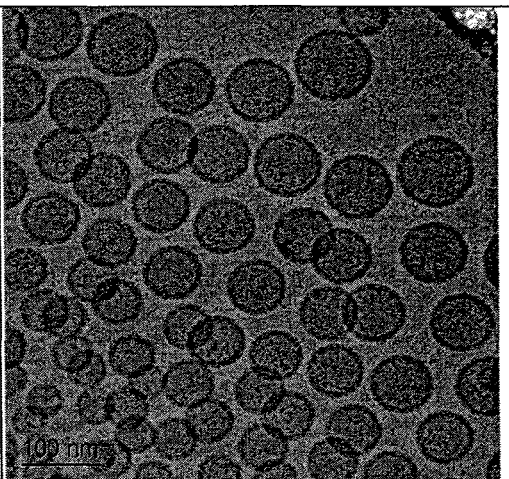
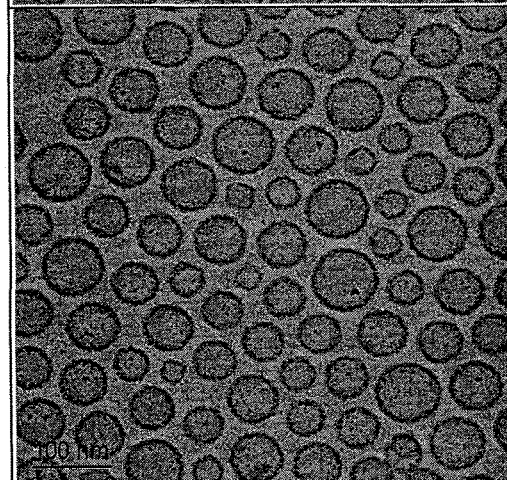
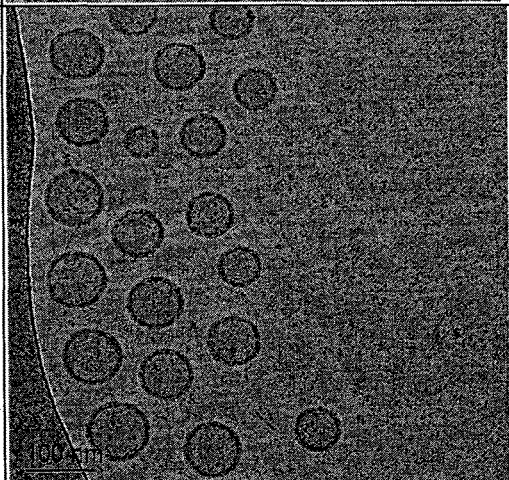
Figure 6C
Figure 6D

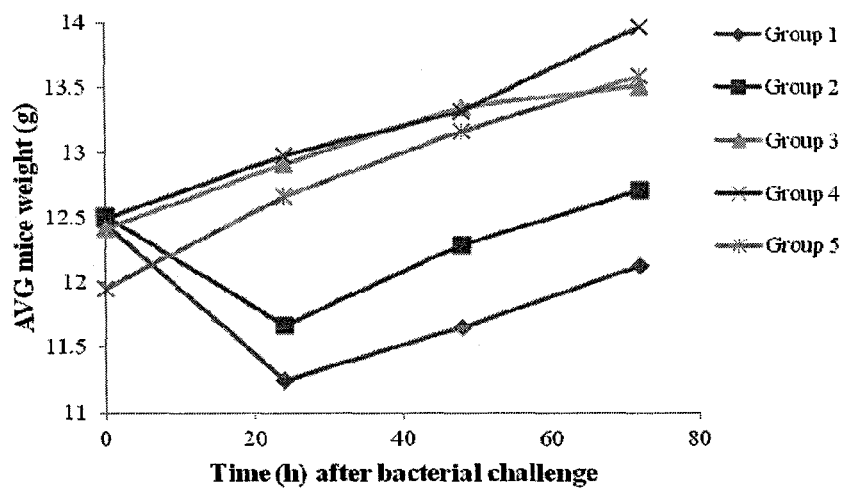
Figure 10
 
Figure 11A          Figure 11B

LIPOSOMAL MUPIROCIN

TECHNOLOGICAL FIELD

The present disclosure relates to drug delivery, in particular to liposomal drug delivery.

BACKGROUND ART

References considered to be relevant as background to the presently disclosed subject matter are listed below:
  McCormack B, Gregoriadis G. 1998. Drugs-in-cyclodextrins-in-liposomes: an approach to controlling the fate of water insoluble drugs in vivo. Int J Pharm 162:59-69
  Clerc S, Barenholz Y. 1995. Loading of amphipathic weak acids into liposomes in response to transmembrane calcium acetate gradients. Biochim Biophys Acta 1240: 257-265.
  Zucker D, Marcus D, Barenholz Y, Goldblum A. 2009. Liposome drugs' loading efficiency: a working model based on loading conditions and drug's physicochemical properties. J Control Release 139:73-80
  Cern A, Barenholz Y, Tropsha A, Goldblum A. 2014. Computer-aided design of liposomal drugs: In silico prediction and experimental validation of drug candidates for liposomal remote loading. J Control Release 173:125-31
  Zhou X, Yung B, Huang Y, Li H, Hu X, Xiang G L R. 2012. Novel liposomal gefitinib (L-GEF) formulations. Anticancer Res 32(7):2919-23
  Noble W C. 1991. The uses and abuses of mupirocin. J Am Acad Dermatol:3-5.
  Cern, A. et al. Quantitative structure-property relationship modeling of remote liposome loading of drugs. J. Control. Release 160, 147-157 (2012)

Acknowledgement of the above references herein is not to be inferred as meaning that these are in any way relevant to the patentability of the presently disclosed subject matter.

BACKGROUND

In order for a liposomal drug to be used clinically, it should be loaded at high concentration per liposome. This is an obligatory requirement in order to provide a therapeutic dose. In most cases, due to the extremely small volume ($\sim 1 \times 10^{-19}$ liter) of nano-liposomes, remote (active) loading of drugs is the only approach to achieve the desired drug concentration. Remote loading uses an ion gradient as the driving force for getting drugs (typically amphipathic weak acids or bases) into preformed liposomes.

Drug remote loading requires sufficient drug solubility, for insoluble drugs or those having low solubility "solubilizers" such as polyethylene glycol (PEG) 400, proplylene glycol (PG), or cyclodextrins such as; hydroxypropyl-β-cyclodextrin (HPCD) may be added during remote loading. So far, the use of cyclodextrins for the enhancement of liposome loading has been studied mainly for drugs loaded by passive loading [Gregoriadis G. Int J Pharm 162:59-69, 1998].

The vast amount of data gathered about remote loading has led to the development of models characterizing the effect of both molecular characteristics and experimental conditions on drug remote loading [Zucker D, Marcus D, Barenholz Y, Goldblum A. 2009. Liposome drugs' loading efficiency: a working model based on loading conditions and drug's physicochemical properties. J Control Release 139: 73-80]. The quantitative structure property relationship (QSPR) models built (Cern, A. et al. Quantitative structure-property relationship modeling of remote liposome loading of drugs. J. Control. Release 160, 147-157 (2012)) allowed drug database screening for identifying good candidates for remote liposomal loading [Cern A, Barenholz Y, Tropsha A, Goldblum A. 2014. Computer-aided design of liposomal drugs: In silico prediction and experimental validation of drug candidates for liposomal remote loading. J Control Release 173:125-31]. One of the drugs identified as a good candidate for loading to liposomes is mupirocin (9-[(E)-4-[(2S,3R,4R,5S)-3,4-dihydroxy-5-[[(2S,3S)-3-[(2S,3S)-3-hydroxybutan-2-yl]oxiran-2-yl]methyl] oxan-2-yl]-3-methylbut-2-enoyl]oxynonanoic acid), an antibiotic, that acts via the inhibition of isoleucyl tRNA synthetase. When absorbed into the blood stream or administered parenterally, mupirocin rapidly degrades to form an inactive monic acid. Thus, hitherto therapy with mupirocin is limited to topical application [Noble W C. 1991. The uses and abuses of mupirocin. J Am Acad Dermatol: Vol. 1, No. 6, Pages 317-319].

In addition, the effect of HPCD in terms of loading by including it in the intra-liposome aqueous phase of pegylated nano-liposomes containing ammonium sulfate and passively loaded with Gefitinib was described. Zhou et al (Anticancer Res 32(7):2919-23 2012) prepared the liposomes as follows (transcribed from the method section in the paper): "A mixture of EPC or HSPC, cholesterol, and mPEG-DSPE (55/40/5 mol/mol), and gefitinib at a lipid to drug weight ratio of 20:1 were dissolved in chloroform and subsequently evaporated at 35° C. to form a thin film. The resulting lipid film was rehydrated with PBS (pH 7.4), 0.3 M $(NH_4)_2SO_4$ solution or 0.3 M $(NH_4)_2SO_4$ plus 0.1 M HPβCD, and incubated at room temperature for 30 min".

GENERAL DESCRIPTION

The present disclosure provides, in accordance with a first of its aspects liposomes comprising a lipid membrane and an intraliposomal compartment, the intraliposomal compartment encapsulating mupirocin, at least one cyclodextrin compound and a pH dependent ionizable anion, said liposomes providing a therapeutic effect upon systemic administration thereof to a subject in need of said effect.

In some embodiments, the intraliposomal compartment also comprises a counter cation (counter to said pH dependent ionizable anion and being part of a highly water miscible salt a further defined herein below).

In some examples, the liposomes have an amount of mupirocin (defined e.g. by its mole ratio with the lipid) and an amount of the at least one cyclodextrin compound (also defined, e.g. by its mole ratio with the lipid) that is sufficient to provide a therapeutic effect upon systemic administration of the liposomes to a subject.

The liposomes disclosed herein are stable liposomes. In some examples, the stability can be determined when kept within a physiologically acceptable medium under storage at 4° C., no more than 20% of mupirocin is released to the medium after storage for a period of at least one month.

The present disclosure also provides liposomes comprising a lipid membrane and an intraliposomal compartment, the intraliposomal compartment encapsulating mupirocin, at least one cyclodextrin compound and a pH dependent ionizable anion, for use in a method for systemic treatment of a subject with said mupirocin.

The present disclosure also provides a pharmaceutical composition comprising a physiologically acceptable carrier suitable for systemic administration, and liposomes within the carrier, the liposomes comprising a lipid membrane and an intraliposomal compartment, said intraliposomal compartment comprising mupirocin, at least one cyclodextrin compound and a pH dependent ionizable anion.

Yet further, there is provided by the present disclosure a method of treating a subject (e.g. one having an infection) with mupirocin the method comprises systemic administration of liposomes comprising a lipid membrane and an intraliposomal compartment, said intraliposomal compartment encapsulating mupirocin, at least one cyclodextrin compound and a pH dependent ionizable anion.

BRIEF DESCRIPTION OF THE DRAWINGS

In order to better understand the subject matter that is disclosed herein and to exemplify how it may be carried out in practice, examples will now be described, by way of non-limiting example only, with reference to the accompanying drawings, in which:

FIG. 6A-6D presents Cryo-TEM images of calcium acetate and calcium acetate-HPCD liposomes containing mupirocin (FIG. 6A and FIG. 6B respectively) versus those containing no drug (FIG. 6C and FIG. 6D respectively)

FIG. 10 presents the average mice weight across the treatment groups over time after bacterial challenge;

FIG. 11A-11D Appearance of untreated mice (FIG. 11A-11B) and liposomal mupirocin treated mice (FIGS. 11C and 11D) 48 h after bacterial challenge.

DETAILED DESCRIPTION

Figure 1:
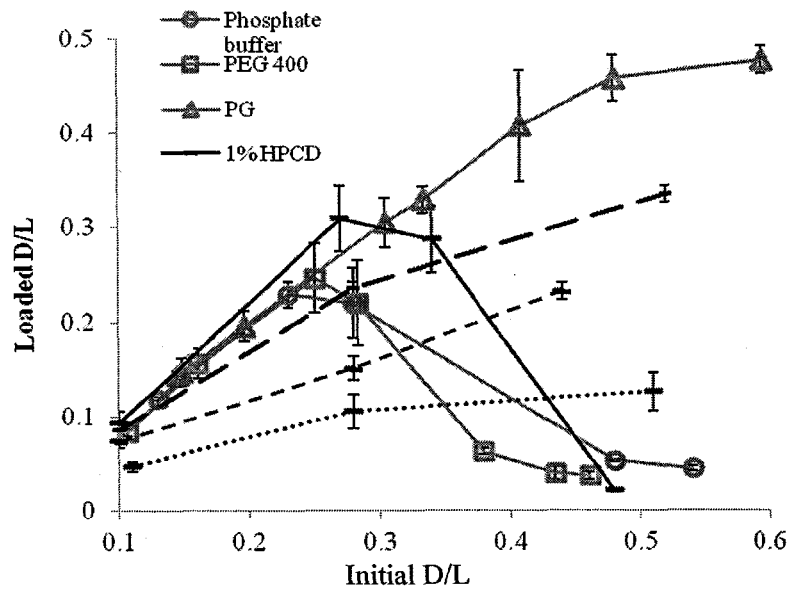
FIG. 1 presents Mupirocin loading (final drug to lipid (D/L) mole ratio) into calcium acetate liposomes as a function of the initial D/L mole ratio and the incubation solution content. (Mean±SE, n=2).

A problem to be solved by the present invention concerns systemic delivery of mupirocin (9-[(E)-4-[(2S,3R,4R,5S)-3, 4-dihydroxy-5-[[(2S,3S)-3-[(2S,3S)-3-hydroxybutan-2-yl] oxiran-2-yl]methyl] oxan-2-yl]-3-methylbut-2-enoyl] oxynonanoic acid), having the chemical formula:

which is known to rapidly degrade in the blood stream and demonstrate high binding to plasma proteins, thus rendering its use confined and limited to topical applications only.

Mupirocin is active in vitro against gram-positive bacteria, including the methicillin-resistant *Staphylococcus aureus* (MRSA) and *Streptococcus pneumoniae*, both considered by the Center of Disease Control (CDC) as serious threats. Among the sensitive gram negative bacteria mupirocin is active against *Neisseria gonorrhoeae* (MIC of 0.05 µg/ml) which is considered as urgent threat by the CDC. Mupirocin mode of action is different from that of other available antibiotics (inhibition of isoleucin tRNA synthase) and therefore, cross resistance with other antibiotics is not expected, making this drug particularly interesting for systemic delivery.

Therefore, there is a need for a formulation clinically acceptable for systemic administration of this drug. To this end, a liposomal formulation of mupirocin was developed, as disclosed herein.

There are many prerequisites in order to achieve a clinically viable formulation based on liposomes for systemic delivery. One is to achieve a sufficient level of drug loading; a second is to maintain the drug in liposomes while circulating in the blood; a third is to release the drug at the target site at a rate and level that is sufficient to result in a desired therapeutic efficacy; and a fourth it so achieve a pharmaceutically accepted product in terms of shelf-life stability.

Liposomal formulation of mupirocin (Nano-mupirocin) may enable its application by systemic administration as the encapsulation in the intra-liposome aqueous phase would protect it from degradation in the blood circulation and enable its passive targeting to the infected tissue taking advantage of the Enhanced Permeability and Retention (EPR) effect in bacterially infected tissues [Azzopardi, E. a, Ferguson, E. L. & Thomas, D. W. The enhanced permeability retention effect: a new paradigm for drug targeting in infection. J. Antimicrob. Chemother. 68, 257-74 (2013)]. However for such a formulation to be efficacious, in addition to accumulation at the infection site, the liposomes should exhibit a controlled slow release of mupirocin in the disease site.

With respect to mupirocin, a further challenge concerned its solubility, as mupirocin is only slightly soluble in aqueous medium and the solubility is pH dependent. As will be shown in the following examples, in phosphate buffer pH 6.3 mupirocin had a solubility of ca 28 mM and this concentration was achieved only after vigorous stirring and sonication. Therefore, attempts have been made to increase the drug solubility using various solubilizers. The results demonstrated that solubility was increased with polyethylene glycol (PEG) 400, proplylene glycol (PG), and the cyclodextrin hydroxypropyl-β-cyclodextrin (HPCD) used as solubilizers.

However, unexpectedly, when attempting to incorporate these solubilizers in the incubation solution used for loading mupirocin into liposome (by the remote loading), the liposomal formulations obtained showed a very fast drug release in serum, which made them unsuitable for clinical use.

In addition, loading of the drug into the liposomes had a bell shape behavior when the drug was loaded from phosphate buffer pH 6.3 or contained PEG400 as solubilizer. The loading pattern from PG solution and HPCD solution was not bell-shaped. However, loading from HPCD solutions was dependent on HPCD concentrations. HPCD (1%) showed slightly higher loaded ratios but a similar bell-shaped loading curve. Higher HPCD concentrations (2.5%-10%) showed constant increase in loaded ratio with increase in the initial ratio, and did not result in a bell-shaped pattern. However, the loaded ratios were higher for 2.5% HPCD and decreased with increasing concentrations of HPCD (5% and 10%); high HPCD concentrations seemed to inhibit loading. When the obtained liposomal formulations were tested for their release profile, it was found that these formulations showed very rapid release in the presence of serum which may not be suitable for clinical use.

Nonetheless, the inventors have successfully developed a liposomal formulation that satisfies all pre-requisites, namely, liposomes having a high drug/lipid ratio, long blood circulation time, a slow release of the drug from the loaded liposomes, long shelf life and most importantly, a formulation that show superior therapeutic efficacy and is suitable for systemic clinical use.

Specifically, based on the inventors' developments, the present disclosure provides a liposome comprising an intraliposomal compartment encapsulating mupirocin, at least one cyclodextrin compound and a pH dependent ionizable anion. As will be shown herein, the amount of mupirocin and the at least one cyclodextrin compound in the liposomes being sufficient to provide a therapeutic effect upon systemic administration of the liposomes to a subject.

The liposomes encapsulating mupirocin can be of any form or size.

In some examples, the liposomes are multilamellar or oligolamellar vesicles.

In some examples, the liposomes are multivesicular vesicles.

In some other examples, the liposomes are unilamellar vesicles.

The liposomes can be small, medium, large or even giant. When referring to small liposomes it is to be understood as having an average size in the range of between about 20 nm-100 nm; when referring to medium sized liposomes, it is to be understood as having an average size in the range of between about 100 nm-200 nm; when referring to large liposomes, it is to be understood as having an average size above about 200 nm; and when referring to giant liposomes (typically giant unilamellar or multivesicular vesicles), it is to be understood as referring to those being larger than 1 μm.

In some examples, the liposomes are small unilamellar vesicles (SUV). In some examples, the SUV have a size distribution of between 20 nm to 100 nm; at times, between 20 nm to 100 nm, further at times, between 40 nm to 100 nm or 50 to 100 nm.

In some examples, the liposomes have an average size of between 60 to 90 nm; at times, between 70 nm to 80 nm; and at times, about 77±5.0 nm.

The liposomes were found to be stable. In fact, it has been found that when within a physiologically acceptable medium, the liposomes encapsulating mupirocin were significantly stable under the storage conditions at 4° C.

When referring to stability in the context disclosed herein it is to be understood that following storage (at 4° C.) for at least a month, no more than 20%, at times, no more than 10% of mupirocin would be released to the storage medium compared to the initial loaded drug. In some examples, the stability of the liposomes is characterized by the fact that no more than 10% of mupirocin is released during storage to the surrounding medium after at least 3 months storage at 4° C. In some examples, the stability of the liposomes is characterized by the fact that no more than 10% of mupirocin is released to the surrounding medium after at least 4 months, 5 months, 6 months, 7 months, 8 months, 9 months, 12 months, and even 24 months under storage at 4° C.

The stability is determined by one or both of chemical and physical stability under storage conditions (4° C., in buffer).

In this context, chemical stability may be examined, inter alia, by one or more of the following parameters:

a) Measurement of dispersion pH (pH meter);

b) phospholipid (PL) acylester hydrolysis by determination of change in non-esterified (free) fatty acids (NEFA) released upon PL hydrolysis [Barenholz et. al. From Liposomes: a practical approach, $2^{nd}$ Edn., RRC New ed, IRL Press Oxford, 1997] or by thin layer chromatography (TLC) [Barenholz, Y. and Amsalem, S. In: Liposome Technology $2^{nd}$ Edn., G. Gregoriadis (Ed.) CRC Press, Boca Raton, 1993, vol. 1, pp: 527-616].

Physical stability of the lipid assemblies may be examined, inter alia, by one or more of the following parameters:

a) assembly size distribution by dynamic light-scattering (DLS).

b) Level of free (non-associated/aggregated) component.

c) zeta potential.

The liposomes are prepared a priori with at least one liposome forming lipid. In the context of the present invention, the term "liposome forming lipids" denotes primarily glycerophospholipids or sphingomyelins that form in water into vesicles, such as, but without being limited thereto, liposomes, as further discussed below.

The liposomes are then characterized, inter alia, by the ratio of each component with respect to the liposome forming lipids. Such components include the drug, namely mupirocin, the at least one CD, and the pH dependent ionizable anion and the counter ion thereto (e.g calcium or sodium acetate).

CD compounds are recognized as cyclic oligosaccharides consisting of (α-1,4)-linked α-D-glucopyranose units and contain a lipophilic central cavity and hydrophilic outer surface. In the context of the present disclosure, the CD can be a naturally occurring CD, as well as derivatives of the naturally occurring CDs. Natural CD include the α-, β-, or γ-cyclodextrin (αCD, βCD or γCD) consisting of six, seven and eight glucopyranose units, respectively. When referring to derivatives of the natural CD it is to be understood as any cyclic oligosaccharides consisting of (α-1,4)-linked α-D-glucopyranose units having a lipophilic central cavity and hydrophilic outer surface.

In some examples, the CD is 2-hydroxypropyl-β-cyclodextrin (HPβCD).

In some examples, the CD is 2-hydroxypropyl-γ-cyclodextrin (HPγCD).

In some examples, the CD is Solfobutyl ether (SBE) cyclodextrin.

In one preferred example, the CD is HPβCD. In some examples, HPβCD is combined with at least one additional solublizer, e.g. an additional CD or co-solvent like propylene glycol.

The liposomes disclosed herein comprise an amount of CD sufficient to allow stability of mupirocin within the liposomes, even when in the presence of serum. Without being bound by theory, it is believed that HPCD interacts with mupirocin in a manner that affects the leakage of the drug from the liposomes, perhaps by complexation. This can be concluded from the DSC images presented herein (FIGS. 9A and 9B) where liposomes containing HPCD exhibit a shift in the melting point of 81.307 for the non-lipid components as compared to the corresponding melting temperature in the absence of HPCD being 78.447 (the lipids have a melting point around 50° C.). In addition, the Cryo-TEM images presented herein show that the liposomes encapsulating mupirocin together with HPCD and calcium as the counter ion had no observable drug crystals inside them. This is in spite of the very high intraliposome concentration of mupirocin which exceed the solubility limit of mupirocin. Mupirocin solubility in calcium acetate 200 mM pH 5.5 was found to be below 2 mg/ml. HPCD (15%) in the medium will increase its solubility to not more than 10 fold. However, the intraliposomal concentration of mupirocin was found to be in the range of 88-108 mg/ml.

Mupirocin intraliposomal concentration was calculated by determination of the intra-liposomal aqueous volume as determined from the intraliposome Ca ions level measured by inductively coupled plasma (ICP), (A. Montaser and D. W. Golightly, eds. (1992). Inductively Coupled Plasmas in Analytical Atomic Spectrometry. VCH Publishers, Inc., New York,). The intraliposomal calcium concentration for 40 mM lipid concentration was found to be 296 mg/L, calcium concentration in the solution used for liposomes preparation was 5812 mg/L. Dividing the two values is the fraction of intraliposomal volume in the formulation (5.09%), corresponding to 1.27 μper μmol of lipid. (for methods to determine trapped volume see Liposomes: a practical approach. edited by R. R. C. New. The Practical Approach Series (Book 58), Oxford University Press, 1990).

As detailed below it has been found that the inclusion within the liposomes of a counter ion to mupirocin increased the stability of the liposomes, and the circulation time of the liposomes in the blood. Specifically, it has been found that liposomes encapsulating mupirocin and in addition to CD also calcium acetate (to provide CA-HPCD-lip) were stable in saline and serum with respect to drug leakage and release rate, as compared to liposomes lacking CD or liposomes lacking the calcium counter ions. Specifically, it has been found that calcium acetate-HPCD liposomes released mupirocin much slower in serum (17-22% after 1 hour) as compared to the release thereof from HPCD-liposomes (not containing calcium acetate) (73% after 1 hour) and the release from calcium acetate liposomes without HPCD (82% released within 1 h). These findings support the understanding that liposomes prepared from medium containing a combination of HPCD and a counter ion gradient, e.g calcium acetate gradient or sodium acetate gradient is essential for establishing clinically suitable liposomes for systemic delivery When referring to "pH dependent ionizable anion" it is to be understood as any salt derived anion that is charged under suitable pH conditions. Thus, it is to be understood that the anion may in fact be in a non-ionized form when in the liposome such that when it is in ionized form, it is retained in the liposome and when in non-ion form, it will pass through the lipid membrane and leak out from the intraliposomal core of the liposome. This will depend on the internal pH, i.e. the pH within the intraliposmal compartment. The salt is one having a high solubility (of at least 250 mM), with the anion being one that has a pKa above 3.5 and a logD at pH 7 in the range between about −2.5 and about 1.5, preferably, in the range between about −1.5 and about 1.0. In some examples, the pH-dependent ionizable anion is selected from the group consisting of acetate, benzoate, formate. In some examples, the anion is an organic anion such as choline. In one particular example, the anion is acetate.

The cation within the salt serve within the liposome as a counter ion to mupirocin. Being a weak amphipathic acid, a suitable counter cation can be an organic as well as inorganic cation. In some examples, the counter cation is selected from the group consisting of calcium, magnesium and sodium. In some examples the cation is counter to the pH dependent ionizable anion, preferably acetate (which is usually the driving force for the remote loading of mupirocin into the liposomes) that has a very low permeability coefficient, preferably $<10^{-11}$.

In some other examples, the counter cation comprises a cationic polymer. Non-limiting examples of cationic polymers include dextrane spermine, dextrane spermidine, aminoethyl dextran, trimethyl ammonium dextran, diethylaminoethyl dextran, polyethyleneimine dextran and the like.

In some particular examples the counter cation is calcium. In some examples, the calcium ion is derived from any one of calcium formate, calcium acetate and calcium benzoate.

In some other examples, the counter cation is sodium, e.g. one derived from sodium acetate, sodium formate and sodium benzoate.

In some examples, the liposomes comprise calcium acetate or sodium acetate.

The liposomes can be characterized by the amount of each component in the liposomal formulation. A more acceptable way to express liposome composition is by the mole ratio between the individual component and the liposome forming lipids (the lipids forming the liposome membrane). In order to determine the mole ratio, the absolute amount of each component in the liposomal formulation is first determined, this being achieved by conventional techniques, known to any person versed in the art. This amount is then translated to moles and the mole ratio with that of the liposome forming lipid(s) is calculated.

In some examples, the at least one CD to lipid mole ratio is between 0.05-2.5, at times, between 0.1 to 2. In some examples, the mole ratio between the at least one CD and lipid is 0.15±0.03.

The concentration of the at least one CD within the liposomal compartment can also be defined (as shown in the non-limiting examples below) and used to characterize the liposomes. In some examples, the concentration of the at least one CD in the intraliposome aqueous phase is at least about 100 mg/ml (corresponding to 73 mM); at times, at least 125 mg/ml (90 mM). In some examples, the concentration of the at least one CD is at most 200 mg/ml (145 mM), at times, at most 175 mg/ml (241 mM). In yet some examples, the concentration of the at least one CD is in the range of 120 mg/ml to 180 mg/ml (87 mM).

In some examples, the concentration of the at least one CD is about 150 mg/ml ±10 mg/ml (about 109 mM).

In some examples, the mole ratio between the ion (the cation or anion) and lipid is between about 0.1 to about 0.5, at times between about 0.2 to 0.4, further at times, the mole ratio is about 0.3±0.05.

Also the concentration of the ion, e.g. the cation (for example calcium and sodium) or anion (e.g. acetate) can be used to characterize the liposomal internal compartment content thereof. In some examples, the concentration of the ion source, (e.g. calcium from calcium acetate and sodium from sodium acetate) is at least 100 mM, at times, 150 mM. In some examples, the concentration of ion source (such as calcium acetate and sodium acetate) is at most 300 mM, at times, at most, 250 mM, or at most 225 mM.

In some examples, the concentration of the ion is about 200 mM.

With respect to the drug per se, in this particular case, mupirocin, the amount thereof entrapped in the liposome is specifically important as it is one of the pre-requisite for clinically acceptable liposomal formulation. To assess drug entrapment, the drug to lipid ratio is determined and compared to an initial ratio (before encapsulation). To this end, drug loaded liposomes are commonly purified to remove unencapsulated drug following drug loading. Then, the amount of drug and the amount of lipid in the liposomes is determined by conventional methods. Based on the determined amounts of the drug and lipid, various parameters are determinable and important to characterize the liposomes: "drug load" which is the grams or moles of drug per grams or mole of lipid; and "entrapment efficiency" expressed as the percentage of drug encapsulated as a function of the initial preload ratio; and "drug to lipid mole ratio" which is the mole of drug per mole of lipid following removal of un-encapsulated drug.

The amount of mupirocin in the liposomes can be determined using commercial chromatography techniques. In some examples, the concentration of mupirocin is determined using a High Performance Liquid Chromatography (HPLC)/UV method based on the U.S Pharmacopea (USP) 35. Mupirocin official monograph; :3962-3]. To calculate the intra-liposomal concentration of mupirocin one also need the aqueous intraliposome trapped volume which can be calculated from the intraliposome calcium concentration (described previously). Mupirocin liposomal concentration in the formulation is determined by HPLC method. Dividing this concentration by the intraliposomal trapped volume will result in intraliposomal mupirocin concentration (see the example for details).

In some examples, the drug load is in the range of 2-10 mg/ml of liposome disperssion. In some examples, the drug load is at least 2 mg/ml; at times, at least 3 mg/ml, at times at least 4 mg/ml, at times at least 5 mg/ml at times at least 6 mg/ml at times at least 7 mg/ml, at times at least 8 mg/ml. In some examples, the drug load is at most 10 mg/ml, at times, at most 9 mg/ml, at times, at most 8 mg/ml at times, at most 7 mg/ml at times, at most 6 mg/ml at times.

In some examples, the drug to lipid mole ratio is determined.

In some examples, the mupirocin/lipid mole ratio is between 0.1 to 1.0; at times, at least 0.1, or at least 0.2, or at least 0.3, or at least 0.4, or at least 0.5, or at least 0.6, or at least 0.7, or at least 0.8, or at least 0.9, or at least 1.0. In some examples, the mole ratio is at most 1.0, or at most 0.9, or at most 0.8, or at most 0.7 or at most 0.6, or at most 0.5, or at most 0.4, or at most 0.3.

In some examples, the mole ratio is between 0.2 to 0.4.

As to the liposome forming lipids, when referring to glycerophospholipids it is to be understood as lipids having a glycerol backbone wherein at least one, preferably two, of the hydroxyl groups at the head group is substituted by one or two of an acyl, alkyl or alkenyl chain, a phosphate group, or combination of any of the above, and/or derivatives of same and may contain a chemically reactive group (such as an amine, acid, ester, aldehyde or alcohol) at the head group, thereby providing the lipid with a polar head group. The sphingomyelins consist of a ceramide unit with a phosphorylcholine moiety attached to position 1 and thus in fact is an N-acyl sphingosine. The phosphocholine moiety in sphingomyelin contributes the polar head group of the sphingomyelin.

In the liposome forming lipids the acyl, alkyl or alkenyl chain is typically between 14 to about 24 carbon atoms in length, and have varying degrees of saturation being fully, partially or non-hydrogenated naturally occurring lipids, semi-synthetic or fully synthetic lipids and the level of saturation may affect rigidity of the liposome thus formed (typically lipids with saturated chains are more rigid than lipids of same chain length in which there are un-saturated chains, especially having cis double bonds).

In some examples, the liposome comprises a single type or a combination of liposome forming lipids.

In some examples, the liposome forming lipid is a phospholipid. When the liposome forming lipid is phospholipid, the amount thereof in the liposome can be determined as organic phosphorous by the modified Bartlett method [Shmeeda H, Even-Chen S, Honen R, Cohen R, Weintraub C, Barenholz Y. 2003. Enzymatic assays for quality control and pharmacokinetics of liposome formulations: comparison with nonenzymatic conventional methodologies. Methods Enzymol 367:272-92].

In some examples, the liposome forming lipid is a choline-type phospholipids such as diacylglycero-phosphocholine (the acyl, alkyl or alkenyl chain being as defined above).

In some other examples, liposome forming lipid is di-lauroyl-sn-glycero-2phosphocholine (DLPC). In some examples, liposome forming lipid is 1,2-dimyristoyl-sn-glycero-3-phosphocholine (DMPC). In some examples, liposome forming lipid is 1,2-dipalmitoyl-sn-glycero-3-phosphocholine (DPPC). In some examples, the liposome forming lipid is 1,2-dipalmitoyl-sn-glycero-3-phosphocholine (DPPC). In some examples, the liposome forming lipid is 1,2-diheptadecanoyl-sn-glycero-3-phosphocholine. In some examples, the liposome forming lipid is 1,2-distearoyl-sn-glycero-3-phosphocholine (DSPC). In some examples, the liposome forming lipid is 1,2-dinonadecanoyl-sn-glycero-3-phosphocholine. In some examples, the liposome forming lipid is 1,2-diarachidoyl-sn-glycero-3-phosphocholine (DBPC). In some examples, the liposome forming lipid is 1,2-dihenarachidoyl-sn-glycero-3-phosphocholine. In some examples, the liposome forming lipid is 1,2-dibehenoyl-sn-glycero-3-phosphocholine 1,2-ditricosanoyl-sn-glycero-3-phosphocholine. In some examples, the liposome forming lipid is 1,2-dilignoceroyl-sn-glycero-3-phosphocholine. In some examples, the liposome forming lipid is 1-myristoyl-2-stearoyl-sn-glycero-3-phosphocholine. In some examples, the liposome forming lipid is 1-palmitoyl-2-stearoyl-sn-glycero-3-phosphocholine (PSPC). In some examples, the liposome forming lipid is 1-stearoyl-2-palmitoyl-sn-glycero-3-phosphocholine (SPPC). In some examples, the liposome forming lipid is 1,2-di-oleoyl-snglycero-3-phosphocholine (DOPC) or di-lauroyl-sn-glycero-2phosphocholine (DLPC).

In some examples, the liposome forming lipid comprises at least hydrogenated soy phosphatidylcholine (HSPC).

In one preferred embodiment, the liposome forming lipid comprises or consists of hydrogenated soy phosphatidylcholine (HSPC).

In some examples the liposome comprises a sterol, such as cholesterol.

In some examples, the liposome comprises a lipopolymer. Lipopolymers comprise lipids modified at their head group with a polymer moiety (PEG) having a molecular weight equal or above 750 Da. The head group may be polar or apolar, to which a large (>750 Da) a flexible hydrophilic polymer is attached. The attachment of the hydrophilic polymer head group to the lipid region may be a covalent or non-covalent attachment, however, is preferably via the formation of a covalent bond (optionally via a linker).

While the lipids modified into lipopolymers may be neutral, negatively charged, as well positively charged, i.e. there is not restriction to a specific (or no) charge. For example the neutral distearoyl glycerol and the negatively charged distearoyl phosphatidylethanolamine, both covalently attached to methoxy poly(ethylene glycol) (mPEG or PEG) of Mw 750, 2000, 5000, or 12000 [Priev A, et al. Langmuir 18, 612-617 (2002); Garbuzenko O., Chem Phys Lipids 135, 117-129(2005); M. C. Woodle and DD Lasic Biochim. Biohys.Acta, 113, 171-199. 1992].

The most commonly used and commercially available lipids derivatized into lipopolymers are those based on phosphatidyl ethanolamine (PE), usually, distearylphosphatidylethanolamine (DSPE). A specific family of lipopolymers employed by the invention include methoxy PEG-DSPE (with different lengths of PEG chains) in which the PEG polymer is linked to the DSPE primary amino group via a carbamate linkage. The PEG moiety preferably has a molecular weight of the head group is from about 750 Da to about 20,000 Da. More preferably, the molecular weight is from about 750 Da to about 12,000 Da and most preferably between about 1,000 Da to about 5,000 Da. One specific PEG-DSPE employed herein is that wherein PEG has a molecular weight of 2000 Da, designated herein $^{2000}$PEG-DSPE or $^{2k}$PEG-DSPE (M. C. Woodle and DD Lasic Biochim. Biohys.Acta, 113, 171-199. 1992).

One particular embodiment in the context of the present disclosure concerns liposomes comprising at least hydrogenated soybean phosphatidylcholime (HSPC), a lipopolymer of 1, 2-distearoyl-sn-glycero-3-phosphoethanolamine-N-[methoxy(polyethylene glycol)-2000] ($^{2k}$PEG-DSPE) and cholesterol.

In some examples, the liposomal membrane comprises at least the liposome forming lipid (which may be one or a combination of such lipids), sterol and the lipopolymer. The mole ratio between these components may vary.

In some examples, the liposomal membrane comprise between 1 mole % to 10 mole % lipopolymer. At times, the liposomal membrane comprises at least 1 mole % lipopolymer; at times, at least 2 mole % lipopolymer, at times, at least 3 mole % lipopolymer, at times, at least 4 mole % lipopolymer, at times, at least 5 mole % lipopolymer, at times, at least 6 mole % lipopolymer, at times, at least 7 mole % lipopolymer, at times, at least 8 mole % lipopolymer. At times, the liposomal membrane comprises at most 8 mole % lipopolymer, at times, at most 7 mole % lipopolymer; at most 6 mole % lipopolymer; at most 5 mole % lipopolymer; at most 4 mole % lipopolymer; at most 3 mole % lipopolymer; at most 2 mole % lipopolymer.

In some examples, the liposomal membrane comprises hydrogenated soy phosphatidyl choline (HSPC), cholesterol and mPEG-DSPE. One particular mole ratio when using this combination of components comprises a mole ratio of the hydrogenated soy phosphatidyl choline (HSPC), cholesterol and mPEG-DSPE being HSPC:cholesterol:mPEG-DSPE of about 55:40:5.

The liposomes comprising in their intraliposomal compartment mupirocin, at least one cyclodextrin compound and a pH dependent ionizable anion are prepared by remote loading of mupirocin into the intra-liposome aqueous phase of the liposomes encapsulating the at least one CD and the anion. These liposomes are referred to herein as the "first population" of liposomes.

Specifically, the first population of liposomes were prepared and these included the at least one CD and a pH dependent ionizable anion. Generally, since the pH dependent ionizable anion, is provided with its pairing counter cation, also the pairing cation is present. For example, when the anion is acetate, it would be appreciated by those versed in the art that calcium or sodium can also be present, being part of the pair calcium or sodium acetate. In some examples, the first population of liposomes was prepared by remote loading with a buffer solution comprising at least the pH dependent ionizable anion and the at least one CD (transmembrane acetate gradient).

The inventors have surprisingly found that the addition of HPCD in the intraliposome aqueous phase slows down mupirocin leakage in serum. Without the HPCD, when incubated in the presence of serum, the drug leakage was very fast and in fact most of the drug leaked into the serum. Without being bound by theory, the inventors believe that the CD interacts with the mupirocin to stabilize the latter in the liposomes.

In some more specific examples, the method of preparing the first population of liposomes comprises rehydration by stirring (preferably at temperature above ambient temperature but below 100° C.) of the lipids to be included in the lipid membrane, e.g. liposome forming lipid, cholesterol, lipopolymer, and the desired amount of the at least one CD (the lipids and CD collectively referred to as the mixture), with a buffer solution containing the desired highly miscible salt (including the pH dependent ionizable anion and counter ion thereto) to thereby form liposomes. Then, if necessary or desired, the liposomes are downsized. Downsizing can be by extrusion and/or or by any other means known to those skilled in the art.

In some examples, the CD weight ratio in the buffer used for rehydration is at least 1%, at times, at least 5%, at times, at least 10%, at times, at least 15%, at times, at least 20%, at times, at least 25%, at times, at least 30%, at times, at least 35%, at times, at least 40%, and at times, up to the limit of its solubility, namely, at least 45%, (the maximum CD solubility)

In some examples, the CD weight ratio in the mixture prior to rehydration by the buffer solution is at most 45%, at times, at most 40%, at most 35%, at most 30%, at most 25%, at most 20%, at most 15%, at most 10%, at most 5%.

In some examples, the first population of liposomes is then dialyzed against a generally recognized and safe (GRAS), none-elecrolyte, buffer solution which would not permeate the liposome bilayer and close to isotonic with the blood. Examples of none-elecrolyte solutions include sugar solutions, such as, without being limited thereto, dextrose, glucose, sucrose. In some particular examples, dialysis is against a sucrose solution. In some examples, dialysis is against a solution comprising 10%±1 sucrose.

The thus formed first population of liposomes is then loaded with mupirocin.

In some examples, loading of mupirocin to the first population of liposomes, comprises remote loading. In some examples, the remote loading is performed by incubating the first population with buffer solution comprising mupirocin. In some examples, the buffer solution holding mupirocin for the loading is a phosphate buffer.

Loading of mupirocin can be with a solution comprising mupirocin at any liposome (in the liposome dispersion forming the first population of liposomes) to mupirocin ratio. In some examples, the liposome to mupricin ratio used for the loading is defined by a volume ratio of between about 1:0.5 to 1:2.0. In some examples, the volume ratio between the liposomes and mupricoin solution is about 1:1.

In some examples, the mupricoin containing buffer solution comprises also the at least one CD. In accordance with some examples, the buffer solution comprise between 1% to 15% of the at least one CD.

In some examples, the buffer solution comprise between 2% to 5% of the at least one CD.

In some examples, the buffer solution for loading mupirocin can comprise other excipients. For example, the buffer solution can comprise, in addition to the at least one CD, one or more solubilizers, such as PG and/or PEG.

The second population of liposomes thus formed are, in accordance with some examples, SUV comprising, encapsulated in the intraliposomal aqueous core, mupirocin, the at least on CD and the pH dependent ionizable anion discussed hereinabove and below.

As shown in the non-limiting examples, loading to CA-HPCD liposomes was higher than loading to other types of liposomes, such as calcium acetate liposomes. Moreover, when using CA-HPCD liposomes, the bell-shaped pattern obtained for loading from phosphate buffer, with other solubilizers, such as PEG 400 disappeared. In order to assess that loading was not driven by the HPCD alone, control HPCD liposomes without calcium acetate gradient were prepared. Loading to these liposomes was much lower and reached a maximal loaded D/L value of 0.1.

Further, the non-limiting examples presented herein show that the liposomes disclosed herein (CA-HPCD liposomes in the Examples) released mupirocin much more slowly in serum (17-22% after 1 h) than other liposomal formulations. Without being bound by theory, it is believed that the release was inhibited by the protection of mupirocin in inclusion complexes that was achieved by HPCD inside liposomes. As further shown in the non-limiting examples, the release from control-HPCD liposomes was more rapid than from calcium acetate-HPCD liposomes (73% after 1 h in serum). The release from calcium acetate liposomes without HPCD was slightly higher (82% released within 1 h) indicating that the combination of HPCD and calcium acetate gradient is important for this purpose.

The present disclosure also provides a pharmaceutical composition comprising a physiologically acceptable carrier suitable for systemic administration, and liposomes being as defined above.

In the context of the present invention, a physiologically acceptable carrier denotes any carrier that is useful in preparing a pharmaceutical composition that is generally safe, non-toxic and neither biologically nor otherwise undesirable. In some examples, the physiologically acceptable carrier is an aqueous based solution suitable for systemic administration. In some examples, the physiologically acceptable carrier suitable for systemic (or parenteral) administration include aqueous and non-aqueous, isotonic sterile injection/infusion solutions, which can contain antioxidants, buffers, bacteriostats, and solutes that render the formulation isotonic with the blood of the intended recipient. In some examples, the carrier is any one or combination of saline, buffered solution, aqueous sugar solutions (dextrose, sucrose etc), etc. In some examples, the carrier may also include thickening agents, stabilizers, and preservatives.

In some examples, the physiologically acceptable carrier comprises a buffering agent. In yet some examples, the buffering agent comprises or is a phosphate buffer.

In some examples, the physiologically acceptable carrier comprises a sugar. In some examples, the sugar is selected from the group consisting of dextrose, glucose and sucrose.

The amount of sugar may vary e.g. depending on the dilution of the composition. However, in some examples, the amount of sugar is determined/defined based on its mole ratio with the liposome forming lipid. In some examples, the sugar to lipid ratio is between about 3 to 6, at times, between about 3.5 to 5. In some examples, the mole ratio is about 4±0.5.

In some examples, the sugar is sucrose and the sucrose to lipid ratio is 4±0.5.

The amount of the mupirocin and the at least one cyclodextrin compound in the liposomes is designed to be sufficient to provide a therapeutic effect upon systemic administration of mupirocin to a subject.

An amount sufficient or effective to achieve a therapeutic effect upon systemic administration is to be understood as including at least one therapeutic effect known to be achieved by or associated with mupirocin. Without being limited thereto the therapeutic effect can be in reducing or elimination an infection. In some examples, the therapeutic effect can be associated with reducing microorganism (bacterial, fungal) load in the treated subject. In some examples, the therapeutic effect can be in reducing or elimination an infection or symptoms associated with an infection caused by gram-positive bacteria. In some examples, the therapeutic effect is against staphylococci and/or streptococci, e.g. *Staphylococcus aureus*. Including the methicillin-resistant *Staphylococcus aureus* (MRSA), *streptococcus pneumonia, N. meningitidis, N. gonorrhoeae, Haemophilus influenza*.

In some examples, the infection is caused by protozoa. In some embodiments, the protozoa is *plasmodium flaciparum*.

The amount of mupirocin to be delivered by the pharmaceutical composition depends on various parameters as known to those skilled in the art and can be determined based on appropriately designed clinical trials (dose range studies) and the person versed in the art will know how to properly conduct such trials in order to determine the effective amount. The amount depends, inter alia, on the type and severity of the disease to be treated and the treatment regime (mode of systemic administration), gender and/or age and/or weight of the treated subject, etc.

In some examples, the pharmaceutical composition is formulated to include a carrier suitable for administration by injection or infusion. In some examples, the administration is by any one of intravenous (i.v.), intramuscular (i.m.), intra-peritoneal (i.p.), and subcutaneous (s.c.) injection.

The present disclosure also provides a method for the administration of treating a subject with mupirocin the method comprises systemic administration of the liposomes as disclosed herein. In accordance with this aspect, also provided by the present disclosure a method of treating a subject having a microbial infection, comprising systemic administration to the subject of the liposomes disclosed herein.

The administration can be by any regimen acceptable for systemic drug delivery. In some examples, the administration is by injection.

Injection of the liposomes disclosed herein was found, as firstly disclosed herein, to be effective, in vivo, in reducing bacterial load. Specifically, Mice in a necrotizing fasciitis model received an injection of group a *streptococcus* (GAS) subcutaneously. Twenty four hours after the bacterial challenge mice which did not receive treatment showed signs of the disease which include rough hair, weight loss, and wound development and in two cases also difficulties in movement and closed eyes. Forty eight hours after the bacterial challenge two of the mice in the un-treated group died. Mice in the group that received free mupirocin (control) did not show mortality but they developed the disease symptoms. However, mice in the liposomal mupirocin group did not develop the disease. Liposomal mupirocin was active even at the prophylactic group that received a single liposomal mupirocin dose 3 h before the bacterial challenge. The study detailed herein showed efficacy of liposomal mupirocin when administered by the parenteral/systemic rout which was superior to the treatment with free mupirocin at lower or equal doses. Mupirocin elimination as can be evaluated based on the activity of the prophylactic dose was slower compared to what is known from literature data of free mupirocin elimination half-life (20-40 min).

In view of the above, in the context of the present disclosure, when referring to treatment by the liposomes disclosed herein, it is to be understood as encompassing ameliorating undesired symptoms associated with a disease, preventing the manifestation of such symptoms before they occur, slowing down the progression of a disease, slowing down the deterioration of symptoms, enhancing the onset of remission period of a disease, slowing down irreversible damage caused in progressive chronic stages of a disease, delaying onset of progressive stages, lessening severity or cure a disease, improving survival rate or more rapid recovery from a disease, preventing the disease from occurring, or a combination of two or more of the above.

The invention will now be described by way of non-limiting examples.

DETAILED DESCRIPTION OF NON-LIMITING EMBODIMENTS AND EXAMPLES

Example 1

Liposome Preparation and Characterization

Materials

Mupirocin (Teva) was a gift from Foamix Ltd (Israel).

Hydroxypropyl-β-cyclodextrin (HPCD) and Dowex 1×8-200 were obtained from Sigma Aldrich.

Hydrogenated soy phosphatidylcholine (HSPC), 1,2-distearoyl-sn-glycero-3-phosphoethanolamine-N-[methoxy (polyethylene glycol)-2000] (mPEG DSPE), and cholesterol were obtained from Lipoid GmbH (Ludwigshafen, Germany).

Sepharose CL-4B was obtained from GE Healthcare.

Adult bovine serum was obtained from Biological Industries (Israel).

The solvents used for analysis were HPLC grade.

All other chemicals were commercial products of reagent grade.

Methods

Preparation of Liposomal Mupirocin

Liposomes were prepared using the calcium acetate (CA) gradient method [Clerc S, Barenholz Y. 1995. Loading of amphipathic weak acids into liposomes in response to trans-membrane calcium acetate gradients. Biochim Biophys Acta 1240:257-265]. Specifically, lipids in a mole ratio of 55:40:5 HSPC: cholesterol: mPEG DSPE were mechanically hydrated by stirring at 65° C. with 200 mM calcium acetate pH 5.5, at a weight ratio of 1:9. The liposomal dispersion was downsized by stepwise extrusion by the Northern Lipids (Burnaby, BC, Canada) extruder using polycarbonate filters starting with 3 times extrusion through a 400 nm pore size membrane, then 3 times through a 100 nm pore size membrane, and finally 10 times through a 50 nm pore size membrane. Liposomes were then dialyzed using a Cellu Sep regenerated cellulose membrane (Membrane Filtration Products, USA), against a 10% sucrose solution. In the case of HPCD-containing liposomes, lipids were hydrated by 200 mM calcium acetate pH 5.5 containing 15% (w/w) HPCD. Control HPCD liposomes were prepared by hydrating lipids with 15% (w/w) HPCD in phosphate buffer 200 mM pH 6.3. All other preparation steps (downsizing and dialysis) were the same as described above. Remote loading was performed by incubating at 65° C. for 10 min a solution of the drug with the liposome dispersion at a volume ratio of 1:1. Liposomes used for loading were freshly prepared and used within one week. Drug loading solutions were prepared in 200 mM phosphate buffer pH 6.3. High mupirocin concentrations in phosphate buffer pH 6.3 (28 mM) were achieved by vigorous stirring and 10 min sonication in a bath sonicator. Loading was also tested from 1 to 10% (w/w) HPCD solutions in phosphate buffer pH 6.3. High mupirocin concentration (28 mM) in 1% HPCD solution was achieved by vigorous stirring and sonication as described for phosphate buffer. Mupirocin solutions in higher HPCD concentrations (2.5-10%) were prepared by stirring only. Loading was also performed from propylene glycol (PG) and from polyethylene glycol (PEG) 400 solutions. In these cases, a stock solution of 100 mM mupirocin was prepared and diluted to the desired concentration with 200 mM phosphate buffer pH 6.3.

Phospholipid concentrations in the liposome dispersions used for loading experiments were in the range of 24-60 mM.

The internal pH of liposomes is measured by the distribution of benzoic acid between the intraliposomal volume and the external volume, the internal pH of calcium acetate liposomes is calculated to be 7.7. Based on previous experience the internal pH of calcium acetate liposomes loaded with drug should be below 7.0

Liposomes were also prepared using sodium acetate gradient with and without 15% (w/w) HPCD. Specifically, lipids in a mole ratio of 55:40:5 HSPC: cholesterol: mPEG DSPE were mechanically hydrated by stirring at 65° C. with 200 mM sodium acetate pH 5.5, at a weight ratio of 1:9. The liposomal dispersion was downsized by stepwise extrusion and then dialyzed as described above. In the case of HPCD-containing liposomes, lipids were hydrated by 200 mM sodium acetate pH 5.5 containing 15% (w/w) HPCD. Loading to sodium acetate liposomes was performed from mupirocin solutions in phosphate buffer 200 mM pH 6.3 as described previously. Note that in the case of sodium acetate, for each sodium there is only one acetate moiety compared to calcium acetate in which for each calcium there are two acetate. Acetate is the driving force for the loading, the lower acetate content in 200 mM sodium acetate compared to 200 mM calcium acetate makes it difficult to compare these two methods in terms of loading efficiencies.

Phospholipid Determination

Phospholipid concentration was determined in the blank liposomes as organic phosphorus by a modified Bartlett method [Shmeeda H, Even-Chen S, Honen R, Cohen R, Weintraub C, Barenholz Y. 2003. Enzymatic assays for quality control and pharmacokinetics of liposome formulations: comparison with nonenzymatic conventional methodologies. Methods Enzymol 367:272-92]. Control HPCD liposomes (containing phosphate buffer) were tested for their phospholipid content by an HPLC method that was based on a procedure for assay of lipid blends, received from Lipoid GmbH. It uses a LiChrospher 100 Diol 5 μm, 250 mm×4.0 mm column, gradient elution with hexane: 2-propanol: water, and evaporative light-scattering detection with an Alltech 3300 ELSD detector.

Mupirocin Quantification

Drug concentrations were quantified using an HPLC/UV method (HPLC system-Hewlett Packard Series II 1090). The column used was a Waters, XBridge C18 column, 5 μm, 4.6 mm×150 mm. The chromatographic conditions were based on a published method [USP 35. Mupirocin official monograph; :3962-3]. A resolution solution for the acid hydrolysis products was prepared according to instructions [USP 35. Mupirocin official monograph; :3962-3]. The resolution between mupirocin hydrolysis products and mupirocin was not less than 2.0. Total (free plus liposomal) drug concentration was determined by HPLC assay of the liposomal dispersion diluted with methanol. Liposomal drug concentration was determined after removing the free drug by mixing the dispersion with Dowex 1×8-200 anion exchanger, which binds the free drug. Intraliposomal mupirocin concentration was calculated by the liposomal drug concentration and the intraliposomal trapped volume (determined by intraliposomal calcium content, described previously) and according to the following equation:

$$\text{Intraliposomsal mupirocin concentration} = \frac{\text{Liposomal mupirocin concentration}\left(\frac{mg}{ml}\right)}{\text{intraliposomal trapped volume (ml) per ml formulation}}$$

Drug to Lipid (D/L) Mole Ratio

The initial D/L ratio refers to the initial mole ratio used for the remote loading. The initial D/L ratio in the incubation was determined as the mole ratio of total amount of drug used for remote loading to total liposomal phospholipid used for remote loading. The loaded D/L ratio refers to the mole ratio between the liposomal drug and phospholipid concentration.

Particle Size Distribution Analysis

Particle size was determined using the well-established dynamic light-scattering method, performed with Zetasizer Nano Series ZEN3600F (Malvern Instruments, Malvern, UK). Mean diameter was based on the volume mean. (For more details see Barenholz Y, Amselem S. 1993. Quality control assays in the development and clinical use of liposome-based formulations. In: G. Gregoriadis (Ed.), Liposome Technology, 2nd ed., Liposome Preparation and Related Techniques; 1993:527-616)

Cryo-TEM Images

Transmission Electron Microscopy (TEM) at cryogenic temperature (Cryo-TEM) was used for direct imaging of solutions and dispersions. Vitrified specimens were prepared on a copper grid coated with a perforated lacy carbon, 300 mesh (Ted Pella, Inc.). A 4 μl drop of the solution was applied to the grid and blotted with filter paper to form a thin liquid film of solution. The blotted samples were immediately plunged into liquid ethane at its freezing point (−183° C.). The procedure was performed automatically in the Plunger (Lieca). The vitrified specimens were transferred into liquid nitrogen for storage. The samples were studied using an FEI Tecnai 12 G2 TEM, at 120 kV with a Gatan cryo-holder maintained at −180° C., and images were recorded on a slow-scan, cooled, charge-coupled device (CCD) Gatan camera. Images were recorded with the Digital Micrograph software package, at low dose conditions to minimize electron beam radiation damage.

Characterization Using Differential Scanning Calorimetry (DSC)

Method

Liposomal mupirocin as disclosed herein were prepared by remote loading using calcium acetate gradient from drug solution in phosphate buffer. Liposomes consisted of 55:40:5 HSPC: cholesterol: mPEG DSPE mole ratio. Two types of liposomes were tested: regular calcium acetate liposomes (CA-liposomes) and liposomes containing in their interior volume 15% hydroxyl propyl beta cyclodextrin (HPCD) in calcium acetate (CA-HPCD-liposomes).

DSC measurement was carried out on DSC-VP (GE Healthcare). The samples and the references were loaded and scanned typically for three cycles (heat, cool and reheat) from 15-20° C. to 90° C. at the speed of 1° C./min. The reference for all the liposomal samples was sucrose: phosphate buffer (1:1). The calcium acetate buffer solution with and without HPCD were served as the references for drug-calcium precipitates with and without HPCD in bulk phase, respectively. The thermograms were corrected by baseline subtraction.

Release Kinetics of Mupirocin from Liposomal Mupirocin

Liposomal mupirocin were incubated following dilution of 1:20 at 37° C. in either 50% adult bovine serum or in saline. Aliquots were taken from these samples at the desired time points and analyzed for level of drug release by gel permeation chromatography (GPC), using a Sepharose CL-4B column, which separates liposomal mupirocin from free mupirocin. The column was equilibrated with saline solution and, following sample loading on column, fractions of 0.5 ml were collected and analyzed for mupirocin content. Mupirocin concentration obtained by HPLC at each fraction was plotted against the volume eluted to obtain an elution profile for each sample. The elution profile contained two peaks; the first corresponded to mupirocin in liposomes and the second to free mupirocin. The area under the curve (AUC) for liposomal mupirocin and free mupirocin was calculated by the trapezoidal method. At each time point the percent drug retained in liposomes (% Retained) was calculated by the following equation:

$$\% \text{ Retained} = \frac{\text{liposomal mupirocin } AUC \text{ at } t = x \times 100}{\text{liposomal mupirocin } AUC \text{ at } t = 0}$$

Results

Effect of Solubilizing Agents on the Remote Loading of Mupirocin into PEGylated Nano-Liposomes Mupirocin loading into PEGylated nano-liposomes exhibiting a transmembrane gradient of calcium acetate (CA-lip) was evaluated using different loading solution compositions. Mupirocin is not freely soluble in aqueous medium. Being a weak acid, its solubility increases with pH. Mupirocin was soluble in phosphate buffer 200 mM pH 6.3 up to a concentration of 15 mM. Higher concentrations were achieved with vigorous stirring and sonication. Improved solubility (ca 100 mM) was achieved with PEG 400 and PG. HPCD solutions of 1-10% w/w in phosphate buffer pH 6.3 also resulted in increased solubility (>34 mM). However, high concentrations (≥28 mM) in 1% HPCD required 10 min sonication in order to achieve a clear solution. It should be noted that the chromatographic profile of mupirocin in the different solutions tested was similar to that of a standard solution. In an attempt to test the effect of solubility enhancers on mupirocin loading, mupirocin was loaded into the liposomes (exhibiting transmembrane calcium acetate gradient) from incubation solutions containing phosphate buffer pH 6.3 with and without PEG 400, PG and, 1-10% HPCD.

FIG. 1 presents loaded D/L ratios as a function of the initial D/L ratios for the different incubation solutions tested. Incubations from phosphate buffer and PEG 400 showed a similar pattern of bell-shaped curves: loaded D/L reached a maximal loaded ratio of 0.23-0.25 D/L and decreased with increase in initial D/L ratios. Loading from PG was high at all initial ratios tested (0.14-0.59) and showed constant increase in loaded D/L, which reached a value of 0.48 for the highest initial ratio tested (0.59). This high loading with PG compared to phosphate buffer and PEG 400 solutions may be a result of PG permeation enhancement characteristics. The loading profile from HPCD solutions was dependent on HPCD concentrations. One % HPCD showed slightly higher loaded ratios but a similar bell-shaped loading curve as for phosphate buffer. Higher HPCD concentrations (2.5-10%) showed constant increase in loaded ratio with increase in the initial ratio, and as for PG, loading from these solutions did not result in a bell-shaped pattern. However, the loaded ratios were higher for 2.5% HPCD and decreased with increasing concentrations of HPCD (5% and 10%); high HPCD concentrations seemed to inhibit loading.

Figure 2:
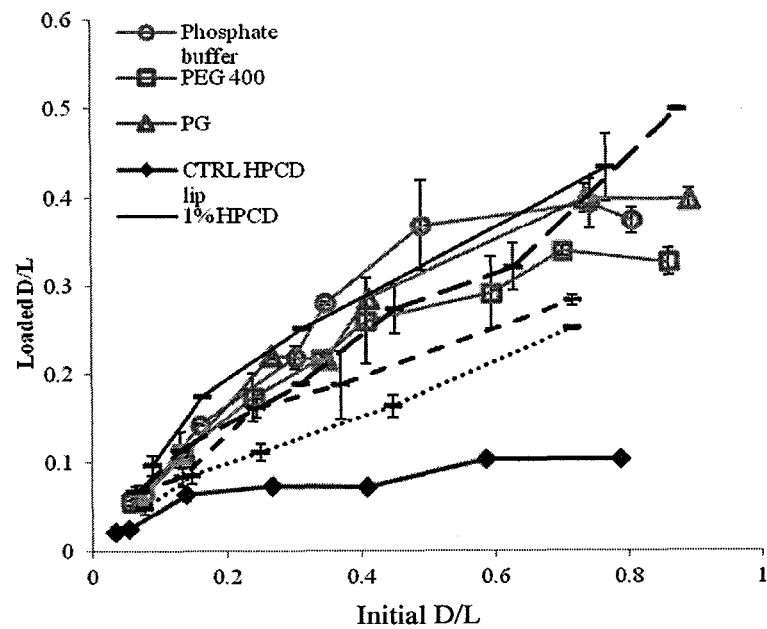
FIG. 2 presents Mupirocin loading into calcium acetate liposomes containing HPCD (CA-HPCD-lip) as a function of the initial D/L mole ratio and incubation solution composition. (Mean±SE, n=2).
Figure 3A:
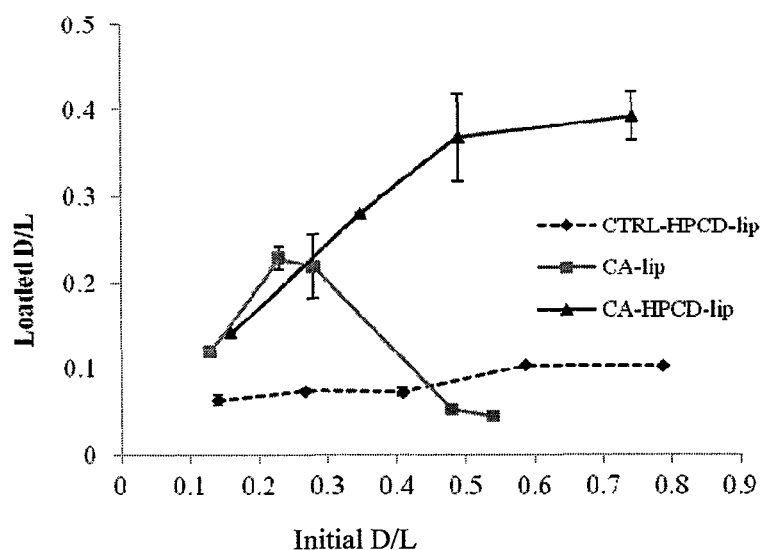
FIGS. 3A-3B present Mupirocin loading from phosphate buffer to liposomes having different intra-liposome aqueous phases, HPCD-liposome, calcium acetate-liposome "CA-lip" or HPCD+calcium acetate liposomes "HPCD-CA-lip" (FIG. 3A) or calcium acetate-liposome "CA-lip", HPCD+calcium acetate liposomes "HPCD-CA-lip", sodium acetate-liposome "SA-lip", or HPCD+sodium acetate liposomes "HPCD-SA-lip" (FIG. 3B), as a function of the initial D/L mole ratio used. (Mean±SE, n=2).
Figure 3B:
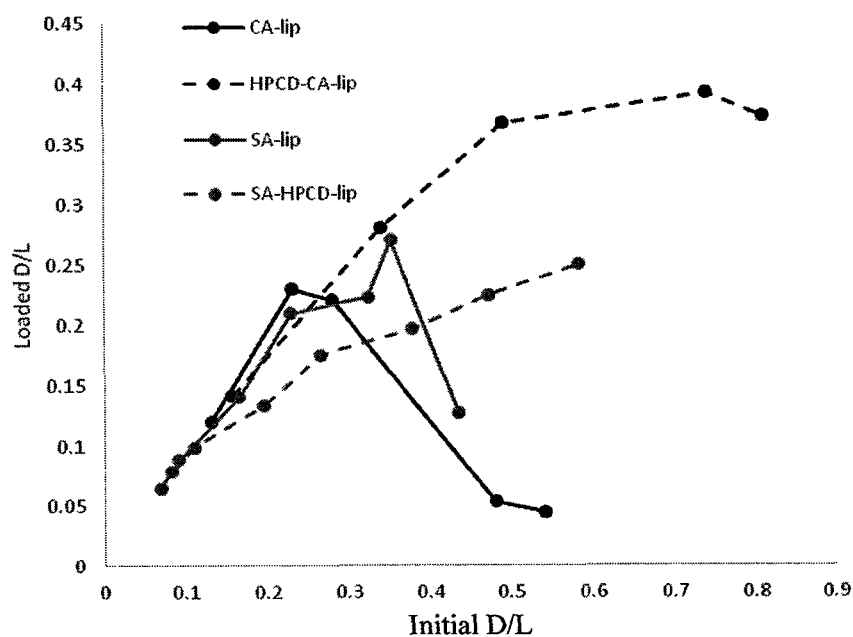

The effect of HPCD on loading was also determined for calcium acetate liposomes containing HPCD in their interior volume (CA-HPCD-lip). PEGylated liposomes were prepared with calcium acetate buffer containing 15% (w/w) HPCD. The HPCD concentration in the liposome interior volume was above the concentration that inhibited loading (10%, see FIG. 1). This concentration inside liposomes, was therefore assumed to aid loading by trapping mupirocin in inclusion complexes inside the liposomes and inhibiting its permeation to the outside medium. FIG. 2 presents loaded D/L ratio in CA-HPCD liposomes as a function of the initial D/L ratio used and incubation solution composition. In addition, control HPCD liposomes (CTRL-HPCD-lip) containing 15% HPCD without using a calcium acetate gradient were also tested for their mupirocin loading from phosphate buffer solution. As presented in FIG. 2, none of the loading solutions to CA-HPCD lip showed a bell-shaped curve. Loading to CA-HPCD-lip was similar to loading to CA-lip (FIG. 1) from incubation solutions which did not show bell-shaped curves for CA-lip (PG and 2.5-10% HPCD). However, a significant difference was found for loading from phosphate buffer, 1% HPCD, and PEG 400. By loading to these CA-HPCD-lip, the bell-shaped loading obtained for CA-lip disappeared. As shown for CA-lip (FIG. 2), loading to CA-HPCD-lip from HPCD solutions was dependent on HPCD concentration; loading decreased with increase in HPCD concentration in the incubation solution. FIG. 2 further shows that for loading to CA-HPCD-lip no solubilizer was required for the incubation solution; phosphate buffer was as good as PG, PEG 400, and 1% HPCD. However, higher HPCD concentrations in the incubation solution (5-10%) decreased loading. FIG. 3A shows comparisons of mupirocin loading from phosphate buffer solution to CA-lip, CA-HPCD-lip, and CTRL-HPCD-lip while FIG. 3B shows comparisons of mupirocin loading from phosphate buffer solution to sodium acetate (NA-acetate) liposomes, NA-acetate-HPCD liposomes, in comparison to the 'calcium acetate' corresponding liposomes. The comparisons demonstrate the influence of the intra-liposome medium on loading pattern. CA-lip showed the bell-shaped loading curve, while this pattern was not observed in HPCD-containing liposomes. However, without a Calcium gradient, the loading was very low. In addition, the result show that there is some preference to the use of calcium acetate over sodium acetate in terms of loading efficiency.

Mupirocin Release

Figure 4:
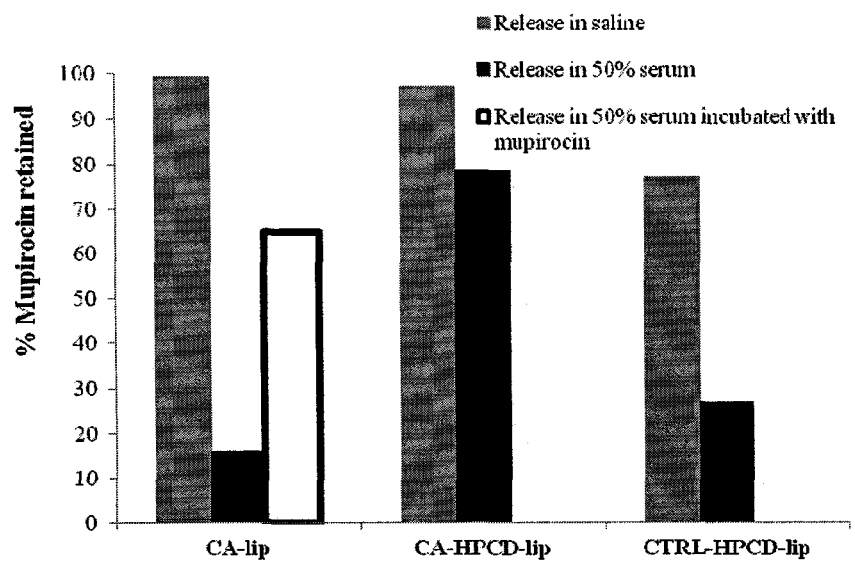
FIG. 4 presents % mupirocin retained in the liposomes following 1 h of incubation at 37° C. of different liposomes (HPCD-liposome, calcium acetate-liposome "CA-lip" or HPCD+calcium acetate liposomes "CA-HPCD-lip").

The release of mupirocin was tested from CA-lip, CA-HPCD liposomes, and control-HPCD liposomes. The release was evaluated in either saline or 50% serum. FIG. 4 shows % mupirocin retained in the liposomes with different intra-liposome media after 1 h of incubation at 37° C. in either saline or serum. CA-lip containing mupirocin were stable in saline but released drug very fast in the presence of 50% serum (82% released within 1 h). There was no effect of the loading solution composition on the release rate; calcium acetate liposomes loaded from PG solution showed a similar value of release in serum compared to liposomes loaded from phosphate buffer (data not shown). However, the release in serum was significantly reduced in CA-HPCD-lip. Following 1 h of incubation only 22% was released, and again, no influence was found for loading solution composition (data not shown). Control HPCD liposomes containing mupirocin showed rapid release (73%) after 1 h of incubation. The substantial difference between mupirocin release from CA-lip in saline and serum was postulated to be attributed to the high protein binding affinity of mupirocin (96.5%). In order to test this assumption, CA-lip containing mupirocin were incubated in serum which was pre-incubated with free mupirocin to a concentration of 12.5 µM. The release from CA-lip in this case was reduced substantially to 35%, supporting our working hypothesis on the involvement of serum protein as a released drug sink.

Figure 5:
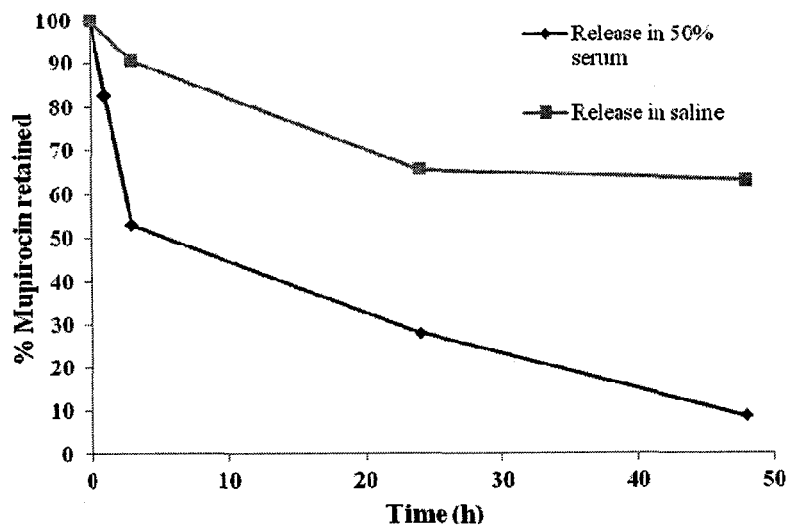
FIG. 5 presents % retained liposomal mupirocin in saline and serum over time from calcium acetate-HPCD liposomes ("CA-HPCD-lip") where each time point represents the liposomal area ratio obtained by the collection of 23 fractions on Sepharose column, as described in the method section (P=0.04, calculated by ANOVA: two factor without replication).
Figure 7A:
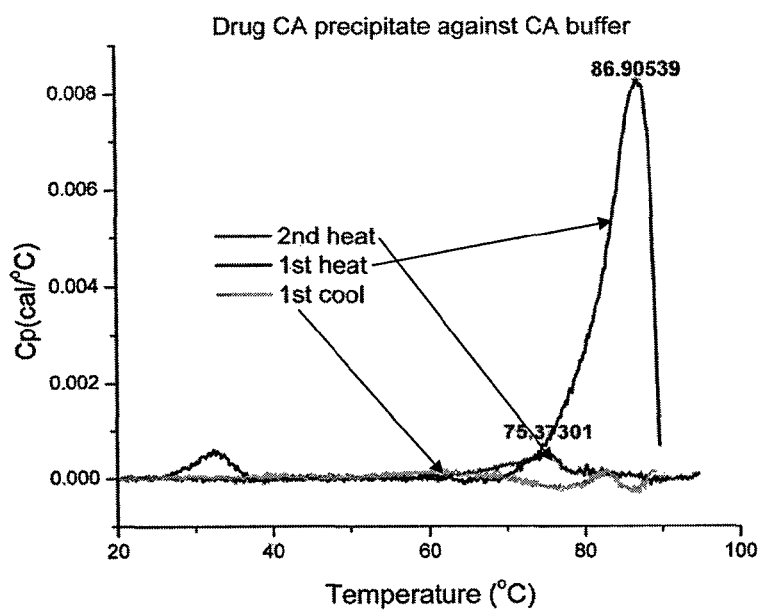
FIG. 7A-7B are thermograms of 1:1 mixtures of drug solution in phosphate buffer with calcium acetate (FIG. 7A) and drug solution with calcium acetate containing 15% HPCD (FIG. 7B)
Figure 7B:
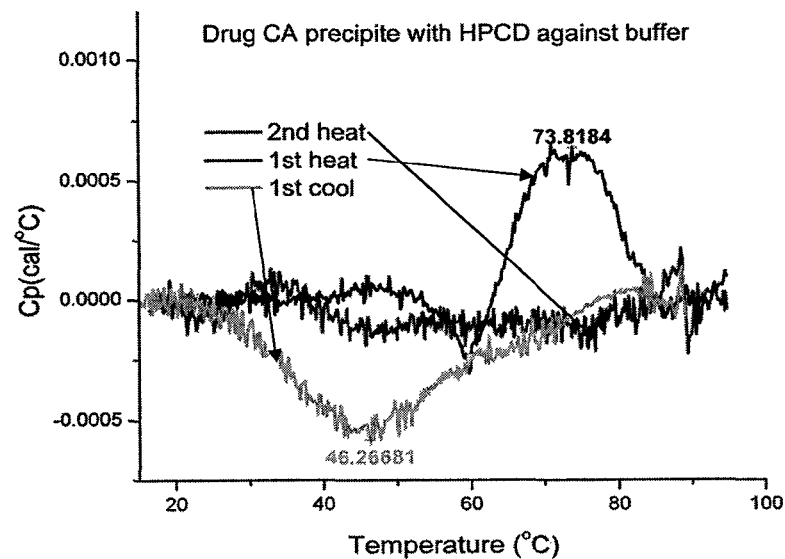

The release profile following 48 h of incubation was tested for CA-HPCD-lip containing mupirocin in the presence of saline and serum (FIG. 5). The release in saline was relatively slow, with 37% release after 48 h of incubation. The release in serum was more rapid, having 47% and 72% release after 3 h and 24 h of incubation, respectively. The release in serum from CA-HPCD-lip was substantially lower than the release from CA-lip (82% release after 1 h of incubation, FIG. 4).

Cryo-TEM Characterization of Liposomal Mupirocin

Cryo-TEM images of CA-lip and CA-HPCD-lip with and without mupirocin are presented in FIG. 6. The images show spherical SUV liposomes with no observable drug crystals inside them or in the liposome medium.

Liposomes Size Distribution

Liposomes were also evaluated for their size and size distribution using the Malvern particle size analyzer. The size obtained was small, Z average of 77±5 nm. The poly-dispersity index (PDI) was lower than 0.05 for all lots prepared, which signifies low variability in the liposomes' size distribution, no difference in size distribution was found between calcium acetate and calcium acetate-HPCD liposomes sodium acetate and sodium acetate-HPCD.

Differential Scanning Calorimetry (DSC) Characterization of Liposomal Mupirocin

Figure 8A:
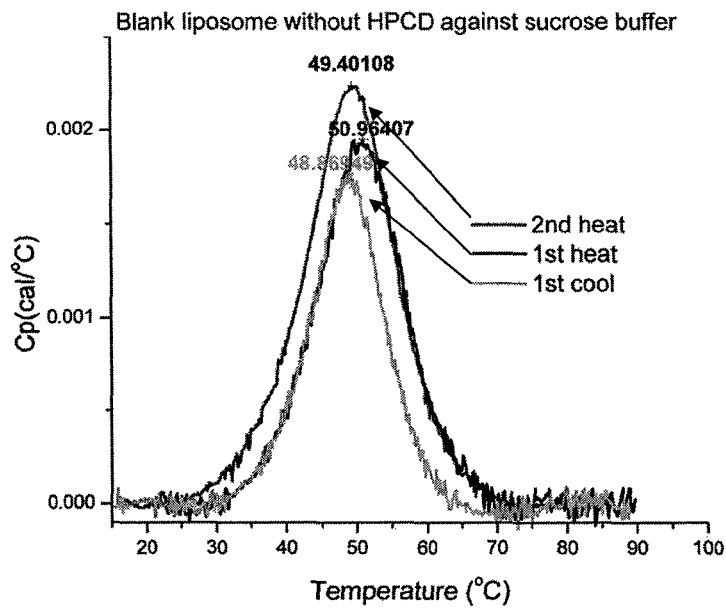
FIG. 8A-8B are thermograms of calcium acetate-liposomes (FIG. 8A) and calcium acetate-HPCD-liposomes (FIG. 8B)
Figure 8B:
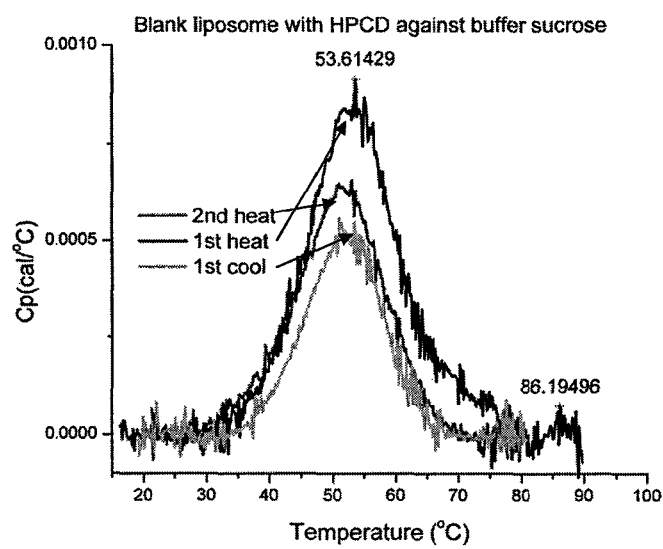

DSC analysis was preformed based on what described by Biltonen and Lichtenberg 1993 (Biltonen R. L. and Lichtenberg D., 1993, Chem. Phys. Lipids 94, 128-142). Blank liposomes with and without HPCD showed one endotherm corresponding to a reversible broad phase transition process with a maximum change of heat capacity at 53° C. which is considered the $T_m$ of the phase transition, (FIGS. 8A-8B), This was in agreement with the phase transition behavior of HSPC based liposomes (Garbuzenko et al 2005 Chem. Phys Lipids se above ref).

In addition, during the period of between 9-24 months no change in the size distribution was exhibited, being indicative of the stability of the liposome.

Finally, Table 1 below summarizes mupirocin liposomal concentration (Concentration) over the indicted time periods (day zero, 9 months, 14 months and 24 months). Drug to lipid mole ratio at zero time point was the mole ratio between the encapsulated drug and lipid concentration in the formulation.

TABLE 1

| | Stability test | | | | |
|---|---|---|---|---|---|
| Preparation No. | I | II | III | IV | V |
| Drug to lipid mole ratio (zero time) | 0.14 | 0.22 | 0.28 | 0.38 | 0.47 |
| Concentration (T = 0) | 0.85 ± 0.01 | 1.30 ± 0.11 | 1.68 ± 0.02 | 4.32 ± 0.29 [a] | 5.40 ± 1.36 [b] |
| Concentration (T = 9 M) | ND | ND | ND | 4.46 ± 0.05 | 6.24 ± 0.56 |
| Concentration (T = 14 M) | 0.90 ± 0.12 | 1.47 ± 0.49 | 1.87 ± 0.20 | ND | ND |
| Concentration (T = 24 M) | ND | 1.53[c] | 1.66 ± 0.43 | ND | ND |

Concentration—in units of mg/ml ± SD
ND—Not determined

Figure 9A:
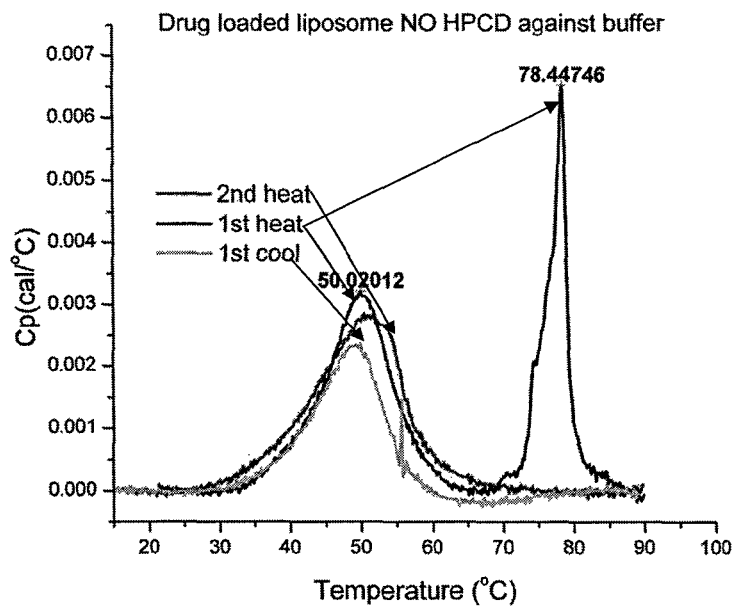
FIGS. 9A-9B are thermograms of calcium acetate-liposomes loaded with mupirocin (FIG. 9A) and calcium acetate-HPCD-liposomes loaded with mupirocin (FIG. 9B)
Figure 9B:
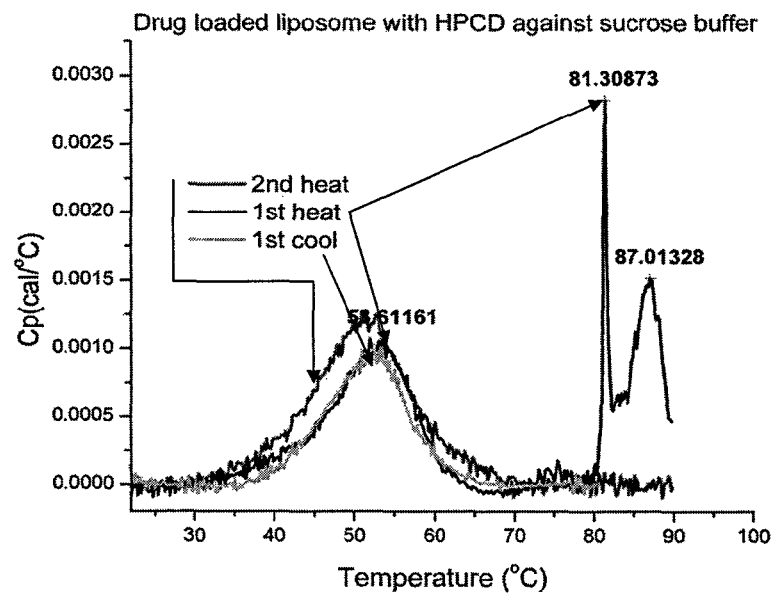

Drug loaded liposomes of identical lipid composition and size distribution to the blank liposomes show two endotherms (FIG. 9A-9B). The first one represent a reversible process a having a $T_m$ similar to this of the blank liposomes and therefore it is attributed to the membrane lipids it was observed for drug loaded liposomes with or without HPCD. The second endotherm at higher temperature (>78° C.) is related to the melting of drug-calcium complex. This endotherm is irreversible which mean once melting of the assembly which involve the drug occurs it does not form the same assembly again upon cooling. Drug complex in calcium acetate liposomes without HPCD had a melting point of 78.4° C. while drug complex in calcium acetate-HPCD liposomes showed two peaks at higher temperatures; 81.3° C. and 87.0° C. which indicate a different complex from that observed without HPCD.

Long Term Stability of Liposomal Mupirocin

Long term stability of liposomal mupirocin was examined based on the visual appearance, encapsulated concentration and particle size distribution, over a period of two years for some of the samples.

Methods

Five liposomal mupirocin formulations prepared by remote loading using calcium acetate gradient and contained HPCD in their interior aqueous phase were followed.

Particle Size and Size Distribution

Particle size measurements were performed using Zetasizer (Malvern Instruments). Mean diameter was based on the volume mean. The size obtained at zero time was 77±1.5 nm. The polydispersity index (PDI) was lower than 0.05.

Determination of Level and Concentration of Liposomal Mupirocin

Mupirocin concentrations in the liposoaml dispersions were quantified using an HPLC/UV method. The column used was a Waters, XBridge C18 column, 5 µm, 4.6 mm×150 mm. The chromatographic conditions were based on a USP method. Liposomal drug concentration was determined after removing the free drug by mixing the dispersion with Dowex 1×8-200 anion exchanger, which binds the free drug.

Results

The visual appearance of the preparations at all time points was translucent with no observed precipitation.

The above results show that the liposomal preparations had no change in size neither in the PDI also, no change in mupirocin concentration in the liposomal dispersion and no liposome aggregation, which are indicative of long term stability.

Example 2

Liposomal Mupirocin in Mice Necrotizing Fasciitis Model

Materials and Methods
Drug Formulations Used in the Study
Liposomes were prepared as described above.
liposomal mupirocin composition is included in Table 1A:

TABLE 1A

| | liposomal dispersion concentration | |
|---|---|---|
| Material | Concentration (mg/ml) | Concentration (mM) |
| HSPC | 28.7 | 36.6 |
| mPEG-DSPE | 9.7 | 3.2 |
| Cholesterol | 9.7 | 25.0 |
| HPCD | 7.6 [a,b] | 5.5 [a,b] |
| Calcium acetate | 1.8 [a,c] | 10.2 [a,c] |
| Mupirocin | 5.5-6.5 | 11.0-13.0 |
| Sucrose | 55 [d, e] | 160.7 |
| Monobasic sodium phosphate | 9.0 [d, e] | 75.0 [d] |
| Disodium phosphate dehydrate | 5.8 [d, e] | 32.6 [d] |

[a] estimate based on trapped liposomal volume in the formulation of 5.09% (calculated based on calcium measurements which are not shown herein).
[b] HPCD concentration in the intraliposomal compartment is 150 mg/ml multiplied by 5.09% trapped liposomal volume resulted in 7.6 mg/ml HPCD in total formulation.
[c] calcium acetate content in the intraliposomal phase is 35.2 mg/ml multiplied by 5.09% trapped liposomal volume results in 1.8 mg/ml calcium acetate in total formulation.
[d] assuming dilution of 0.53 with loading solution (based on phospholipid concentration obtained after diafiltration).
[e] The osmolality of the final formulation was below 400 mOsm/kg Liposomal mupirocin concentration as determined by HPLC/UV method after separation of free mupirocin with Dowex 1×8-200 (anion exchanger) was 5.5-6.5 mg/ml.

The intraliposomal concentration of HPCD, calcium acetate and mupirocin were determined, as shown in Table 1B. HPCD:mupirocin intraliposomal mole ratio was found to be in the range of 0.6-0.8.

TABLE 1B

| | intraliposomal content: | |
|---|---|---|
| Component | Concentration (mg/ml) | Concentration (mM) |
| HPCD | 150 | 109 |
| Calcium | 35 | 200[a, b] |
| Mupirocin | 88-108[c] | 177-216 |

[a] Corresponding to 20.4 μmol acetate in the intraliposomal volume before loading
[b] Initial acetate concentration before loading was 400 mM and after loading it was reduced to approx. 200 mM
[c] Calculated based on liposomal mupirocin concentration in the formulation of 4.5-5.5 mg/ml concentrated in 5.09% intra-liposomal volume Free Mupirocin Solution Free mupirocin solution (6 mg/ml) was prepared in phosphate buffer 200 mM pH 6.3.

In Vivo Study Procedure

Necrotizing fasciitis model was performed based on a published method [Hidalgo-grass, C. et al. Mechanisms of disease Effect of a bacterial pheromone peptide on host chemokine degradation in group A streptococcal necrotising soft-tissue infections. 363, (2004)]. Specifically the working protocol included:

Female BALB/c mice, 10 g weight and at the age of 3-4 weeks were selected.

$1^{st}$ Day: Bacteria were seeded on blood-agar plates and incubated at 37° C. THY medium was prepared, autoclaved and kept at room temperature.

$2^{nd}$ Day: plates were taken from the incubator and placed at room temperature.

$4^{th}$ Day: bacteria were transferred from the plates to 5 ml THY tube (warmed in the incubator).

$5^{th}$ Day: 2 ml bacteria were transferred from the 5 ml THY tube to 50 ml THY tube. Bacteria were grown to early logarithmic phase ($O.D_{600}$=0.3-0.4), washed with PBS and suspended in PBS to $O.D_{600}$=0.8 which correlates to $10^8$ bacteria in injected volume of 100 μl. The obtained bacteria volume was divided to vials according to the number of mice in the study. Each dilution was seeded on blood agar plates and counting colonies on the day after.

Analysis:

On the $5^{th}$ day, mice hair was removed from the center of mice back and bacteria were injected subcutaneously.

$6^{th}$-$7^{th}$ Days: Disease state and mice mortality were followed. Mice that survive these days were sacrificed. Disease condition was followed according to the Table 2A below.

Table 2B presents the study groups. Specifically, Group A streptococcus (GAS) injection ($0.75 \times 10^8$ CFU) was administered to all study groups. The drug was administered by IV injection of 100 μl formulation. Each liposomal mupirocin dose was 45 mg/kg. Each free mupirocin dose was 50 mg/kg.

TABLE 2A

| | Score Parameters | | | | | | |
|---|---|---|---|---|---|---|---|
| Parameter | Score 0 | Score 1 | Score 2 | Score 3 | Score 4 | Score 5 | Score for animal sacrifice |
| Eye appearance | Open | Half-open | Closed | NA | NA | NA | 2 |
| Movements | Regular | Slightly difficult | No movements | NA | NA | NA | 1-2 |
| Hair appearance | Regular | Slightly rough hair | Rough hair | NA | NA | NA | 1-2 |
| Wound appearance | Without wound | Small wound | Medium-small wound | Medium wound | Substantial wound | Deep/substantial wound | 4-5 |
| Wound size | | 0.2-0.35 cm | 0.35-0.6 cm | 0.6-0.8 cm | 0.8-1.0 cm | 1.0-1.4 cm | |
| % weight decrease in the first 24 h | | <5% | 5-8% | 8-10% | 10-15% | >15% | 4-5 |

TABLE 2B

| | Study groups | | | | |
|---|---|---|---|---|---|
| Group no. | GAS injection | Treatment | Dosing schedule | Total mupirocin dose administered (mg/kg/day) | No. mice |
| 1 | $0.75 \times 10^8$ CFU | Un-treated (no drug administration) | None | None | 6 |
| 2 | $0.75 \times 10^8$ CFU | Free drug | 3 h before bacterial challenge and 3 and 24 h after bacterial injection | 150 | 6 |
| 3 | $0.75 \times 10^8$ CFU | Liposomal mupirocin | 3 h before bacterial challenge | 45 | 6 |
| 4 | $0.75 \times 10^8$ CFU | Liposomal mupirocin | 3 h before bacterial challenge and 3 h after bacterial injection | 90 | 6 |
| 5 | $0.75 \times 10^8$ CFU | Liposomal mupirocin | 3 h before bacterial challenge and 3 and 24 h after bacterial injection | 135 | 6 |

Results

Mice were evaluated based on the parameters found in the study procedure described above. The observation results are summarized in Tables 3-9. Mice in Group 1 (untreated, no drug administration) and Group 2 (free drug) developed the disease 24 h after bacteria challenge.

In the untreated group, 2 of the mice were very ill (more than other mice in this group) as was shown by their eyes which were closed or partially closed and their difficulties in movements. These two mice died at the next observation point (48 h). All other mice in this group and in group 2 developed a disease which was less severe: they reduced weight in the first 24 h, they had a wound and their hair was rough and not smooth.

Figure 11C:
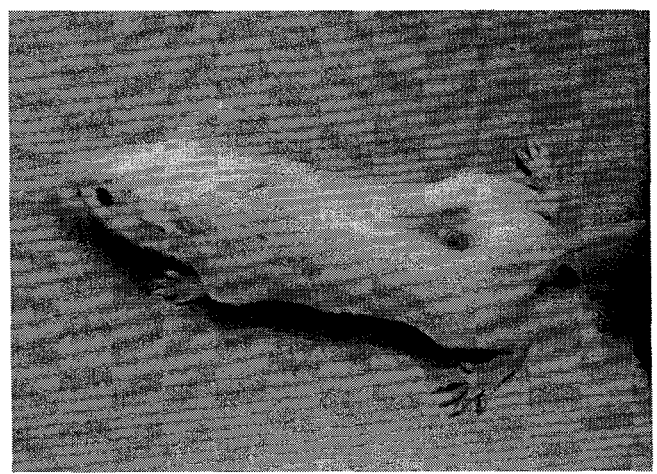
Figure 11D:
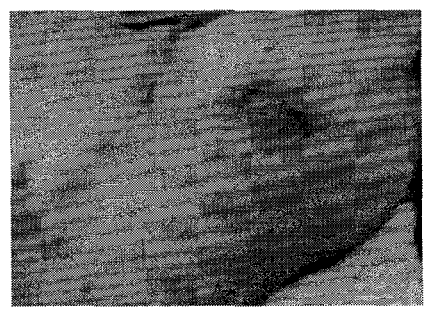

Mice in groups 3-5 that received liposomal mupirocin did not show symptoms of the disease even in group 3 that received only one prophylactic dose (3 h before bacterial injection). FIG. 10 presents the average mice weight over the study. As can be seen from the Figure mice in groups 3-5 gain weight throughout the study as opposed to groups 1 and 2 which showed decrease in weight at the first 24 h. FIGS. 11A and 11B present pictures of mice in the un-treated group and liposomal mupirocin group 48 h after bacterial injection.

TABLE 3

Mice mortality across study groups per time point

| Group no. | Time (h) after bacterial challenge | | | |
|---|---|---|---|---|
| | 24 | 48 | 72 | 96 |
| 1 | 0 | 2/6 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |

TABLE 4

Average mice weight (g) at each time point

| Group no. | Time (h) after bacterial challenge | | | |
|---|---|---|---|---|
| | 24 | 48 | 72 | 96 |
| 1[a] | 12.5 | 11.3 | 11.7 | 12.1 |
| 2[b] | 12.5 | 11.7 | 12.3 | 12.7 |
| 3[b] | 12.4 | 12.9 | 13.4 | 13.5 |
| 4[b] | 12.5 | 13.0 | 13.3 | 14.0 |
| 5[b] | 12.0 | 12.7 | 13.2 | 13.6 |

[a] Six mice in group 1 at 24 h. Four mice at 48, 72 and 96 h.
[b] Six mice per group

TABLE 5

Average mice weight change (%) 24 h after bacteria challenge (6 mice per group)

| Group no. | % weight change |
|---|---|
| 1 | −10 |
| 2 | −7 |
| 3 | 4 |
| 4 | 4 |
| 5 | 6 |

TABLE 6

Hair appearance at each time point

| Group No. | Time (h) after bacterial challenge | | | |
|---|---|---|---|---|
| | 24 | 48 | 72 | 96 |
| 1[a] | Rough hair | Rough hair | 2 mice with rough hair all other with regular smooth hair | Regular smooth hair |
| 2[b] | Rough hair | Rough hair | One mouse with rough hair all other with regular smooth hair | Regular smooth hair |
| 3[b] | 2 mice with rough hair all other with regular smooth hair | Regular smooth hair | Regular smooth hair | Regular smooth hair |
| 4[b] | Regular smooth hair | Regular smooth hair | Regular smooth hair | Regular smooth hair |
| 5[b] | Regular smooth hair | Regular smooth hair | Regular smooth hair | Regular smooth hair |

[a] Six mice in group 1 at 24 h. Four mice at 48, 72 and 96 h.
[b] Six mice per group

TABLE 7

Wound appearance at each time point

| Group No. | Time (h) after bacterial challenge | | | |
|---|---|---|---|---|
| | 24 | 48 | 72 | 96 |
| 1[a] | 2 mice with small wound. All others without wound | All with big wound | All with big wound | All with big wound |
| 2[b] | No wound | All with small wound | All with small wound | All with small wound |
| 3[b] | No wound | No wound | No wound | No wound |
| 4[b] | No wound | No wound | No wound | No wound |
| 5[b] | No wound | No wound | No wound | No wound |

[a] Six mice in group 1 at 24 h. Four mice at 48, 72 and 96 h.
[b] Six mice per group

TABLE 8

Eyes appearance at each time point

| Group No. | Time (h) after bacterial challenge | | | |
|---|---|---|---|---|
| | 24 | 48 | 72 | 96 |
| 1[a] | 2 mice- closed/half closed eyes. All others with open eyes | Open eyes | Open eyes | Open eyes |
| 2[b] | Open eyes | Open eyes | Open eyes | Open eyes |
| 3[b] | Open eyes | Open eyes | Open eyes | Open eyes |
| 4[b] | Open eyes | Open eyes | Open eyes | Open eyes |
| 5[b] | Open eyes | Open eyes | Open eyes | Open eyes |

[a] Six mice in group 1 at 24 h. Four mice at 48, 72 and 96 h.
[b] Six mice per group

TABLE 9

Description of mice movement at each time point

| Group no. | Time (h) after bacterial challenge | | | |
|---|---|---|---|---|
| | 24 | 48 | 72 | 96 |
| 1[a] | 2 mice- slightly difficult movement. All others show | One mouse- slightly difficult movement. All others show | Regular | Regular |

TABLE 9-continued

Description of mice movement at each time point

Time (h) after bacterial challenge

| Group no. | 24 | 48 | 72 | 96 |
|---|---|---|---|---|
| 2 [b] | regular movement Regular | regular movement Regular | Regular | Regular |
| 3 [b] | Regular | Regular | Regular | Regular |
| 4 [b] | Regular | Regular | Regular | Regular |
| 5 [b] | Regular | Regular | Regular | Regular |

[a] Six mice in group 1 at 24 h. Four mice at 48, 72 and 96 h.
[b] Six mice per group

The invention claimed is:

1. Liposomes comprising:
a lipid membrane; and
an intraliposomal aqueous compartment, the intraliposomal compartment encapsulating mupirocin, at least one cyclodextrin CD compound and a pH-dependent ionizable anion,
wherein said liposomes have a mupirocin to lipid mole ratio within the range of 0.1 to 1.0, and said liposomes provide a therapeutic effect upon systemic administration thereof to a subject in need of said effect.

2. The liposomes of claim 1, comprising said at least one CD in a CD to lipid mole ratio within the range of 0.05 to 2.5.

3. The liposomes of claim 1, wherein the at least one cyclodextrin compound is 2-Hydroxypropyl-β-cyclodextrin (HPβCD).

4. The liposomes of claim 1, comprising said pH dependent ionizable anion in an ion to lipid mole ratio within the range of 0.1-0.5.

5. The liposomes of claim 1, wherein the pH dependent ionizable anion is acetate.

6. The liposomes of claim 1, comprising said mupirocin in a mupirocin to lipid mole ratio within the range of 0.2 to 0.4.

7. Liposomes comprising:
a lipid membrane; and
an intraliposomal compartment encapsulating mupirocin, at least one cyclodextrin compound and a pH dependent ionizable anion,
wherein said liposomes have a mupirocin to lipid mole ratio within the range of 0.1 to 1.0.

8. The liposomes of claim 7, comprising said at least one CD in a CD to lipid mole ratio within the range of 0.05 to 2.5.

9. The liposomes of claim 7, wherein the at least one cyclodextrin compound is selected from the group consisting of 2-Hydroxypropyl-β-cyclodextrin (HPβCD).

10. The liposomes of claim 7, comprising said pH dependent ionizable anion in an ion to lipid mole ratio within the range of 0.1-0.5.

11. The liposomes of claim 7, wherein the pH dependent ionizable anion is acetate.

12. The liposomes of claim 7, comprising said mupirocin in a mupirocin to lipid mole ratio within the range of 0.2 to 0.4.

13. A pharmaceutical composition comprising:
a physiologically acceptable carrier suitable for systemic administration; and
liposomes within the carrier, the liposomes comprising a lipid membrane and an intraliposomal compartment, said intraliposomal compartment comprising mupirocin, at least one cyclodextrin compound and a pH dependent ionizable anion, wherein said liposomes have a mupirocin to lipid mole ratio within the range of 0.1 to 1.0.

14. The pharmaceutical composition of claim 13, wherein said physiologically acceptable carrier comprises sucrose.

15. A method of treating a subject with mupirocin comprising:
administering, systemically, liposomes comprising a lipid membrane and an intraliposomal compartment, said intraliposomal compartment encapsulating mupirocin, at least one cyclodextrin compound and a pH dependent ionizable anion, wherein said liposomes have a mupirocin to lipid mole ratio within the range of 0.1 to 1.0.

16. The method of claim 15, wherein said administration comprises parenteral administration.

17. A method of treating a subject having a microbial infection, the method comprising systemic administration of liposomes comprising a lipid membrane and an intraliposomal compartment, the intraliposomal compartment encapsulating mupirocin, at least one cyclodextrin compound and a pH dependent ionizable anion, wherein said liposomes have a mupirocin to lipid mole ratio within the range of 0.1 to 1.0.

18. The method of claim 17, for treating an infection caused by a bacteria selected from the group consisting of streptococcus, streptococcus pneumonia, Staphylococcus aureus, N. meningitidis, N. gonorrhoeae, Haemophilus influenza.

* * * * *